United States Patent
Collier et al.

(10) Patent No.: US 12,290,603 B2
(45) Date of Patent: May 6, 2025

(54) TABLETIZATION OF PEPTIDE SELF-ASSEMBLIES AND METHODS OF MAKING AND USING THE SAME

(71) Applicant: Duke University, Durham, NC (US)

(72) Inventors: Joel Collier, Durham, NC (US); Sean Kelly, Durham, NC (US)

(73) Assignee: Duke University, Durham, NC (US)

( * ) Notice: Subject to any disclaimer, the term of this patent is extended or adjusted under 35 U.S.C. 154(b) by 562 days.

(21) Appl. No.: 17/764,406

(22) PCT Filed: Sep. 28, 2020

(86) PCT No.: PCT/US2020/053095
§ 371 (c)(1),
(2) Date: Mar. 28, 2022

(87) PCT Pub. No.: WO2021/062374
PCT Pub. Date: Apr. 1, 2021

(65) Prior Publication Data
US 2022/0362159 A1 Nov. 17, 2022

Related U.S. Application Data

(60) Provisional application No. 62/906,893, filed on Sep. 27, 2019.

(51) Int. Cl.
| | |
|---|---|
| A61K 9/20 | (2006.01) |
| A61K 9/00 | (2006.01) |
| A61K 47/60 | (2017.01) |
| A61K 47/69 | (2017.01) |

(52) U.S. Cl.
CPC .......... *A61K 9/2095* (2013.01); *A61K 9/0056* (2013.01); *A61K 9/2018* (2013.01); *A61K 47/60* (2017.08); *A61K 47/6929* (2017.08)

(58) Field of Classification Search
None
See application file for complete search history.

(56) References Cited

U.S. PATENT DOCUMENTS

| | | | |
|---|---|---|---|
| 4,001,944 A | 1/1977 | Williams | |
| 4,371,516 A | 2/1983 | Gregory et al. | |
| 4,616,047 A | 10/1986 | Lafon | |
| 4,946,684 A | 8/1990 | Blank et al. | |
| 6,207,749 B1 | 3/2001 | Mayes et al. | |
| 9,200,082 B2 | 12/2015 | Collier et al. | |
| 9,241,987 B2 | 1/2016 | Collier et al. | |
| 9,849,174 B2 | 12/2017 | Collier et al. | |
| 10,596,238 B2 | 3/2020 | Collier et al. | |
| 11,246,924 B2 | 2/2022 | Collier et al. | |
| 2007/0087114 A1 | 4/2007 | Chilkoti et al. | |
| 2010/0292130 A1 | 11/2010 | Skerra et al. | |
| 2014/0273148 A1 | 9/2014 | Collier et al. | |
| 2016/0074509 A1 | 3/2016 | Collier et al. | |
| 2022/0194989 A1 | 6/2022 | Collier et al. | |
| 2022/0387605 A1 | 12/2022 | Collier et al. | |

FOREIGN PATENT DOCUMENTS

| | | |
|---|---|---|
| EP | 2173890 A1 | 4/2010 |
| GB | 2111423 A | 7/1983 |
| WO | 2008039483 A2 | 4/2008 |
| WO | 2008155134 A1 | 12/2008 |
| WO | 2009091518 A2 | 7/2009 |
| WO | 2011063264 A1 | 5/2011 |
| WO | 2012177868 A1 | 12/2012 |
| WO | 2017173398 A1 | 10/2017 |
| WO | 2019018572 A1 | 1/2019 |
| WO | 2023044163 A2 | 3/2023 |

OTHER PUBLICATIONS

GenBankAccession No. XP_064100865, 2024, 2 pages.
Xu K, Acharya P, Kong R, et al. Epitope-based vaccine design yields fusion peptide-directed antibodies that neutralize diverse strains of HIV-1. Nat Med. Jun. 2018:1-19.
Yenkoidiok-Douti, L.; Jewell, C. M., Integrating Biomaterials and Immunology to Improve Vaccines Against Infectious Diseases. ACS Biomaterials Science & Engineering 2020.
Zhang L. The Immunogenicity and Immunoprotection of VBP3 Multi-epitope Vaccine Targeting Angiogenesis and Tumor Inhibition in Lung Cancer- Bearing Mice. International Journal of Peptide Research and Therapeutics. 2019;25(1):215-225.
Zieglmayer P, Focke-Tejkl M, Schmutz R, et al. Mechanisms, safety and efficacy of a B cell epitope-based vaccine for immunotherapy of grass pollen allergy. EBIOM. 2016; 11(C):43-57.
United States Patent and Trademark Office, Office Action for U.S. Appl. No. 17/608,443, mailed Sep. 10, 2024.
Adar Y, Singer Y, Levi R, et al. A universal epitope-based influenza vaccine and its efficacy against H5N1. Vaccine. 2009;27(15):2099-2107.
Ali et al., Application of biorelevant saliva-based dissolution for optimisation of orally disintegrating formulations of felodipine, International Journal of Pharmaceutics, v. 555, 2019, p. 228-236.
Banskota et al. "Long circulating genetically encoded intrinsically disordered zwitterionic polypeptides for drug delivery." Biomaterials vol. 192 (2019): 475-485.
Banskota S, Saha S, Bhattacharya J, Kirmani N, Yousefpour P, Dzuricky M, Zakharov N, Li X, Spasojevic I, Young K, Chilkoti A. Genetically Encoded Stealth Nanoparticles of a Zwitterionic Polypeptide-Paclitaxel Conjugate Have a Wider Therapeutic Window than Abraxane in Multiple Tumor Models. Nano Lett. Apr. 8, 2020;20(4):2396-2409.
Chandrasekhar, R.; Hassan, Z.; AlHusban, F.; Smith, A. M.; Mohammed, A. R., The role of formulation excipients in the development of lyophilised fast-disintegrating tablets. European journal of pharmaceutics and biopharmaceutics 2009, 72 (1), 119-129.

(Continued)

*Primary Examiner* — Nannette Holloman
(74) *Attorney, Agent, or Firm* — Quarles & Brady, LLP

(57) ABSTRACT

The present disclosure provides, in part, peptide self-assemblies that are made into tablet form and methods of making and using the same. In some embodiments, the disclosure provides methods and formulations for a tabletized form of a vaccine, particularly a vaccine comprising self-assembling peptide-polymer nanofibers, an excipient and an adjuvant. Methods of making and using the tablet formulation are also provided.

20 Claims, 18 Drawing Sheets

Specification includes a Sequence Listing.

(56) References Cited

OTHER PUBLICATIONS

Chen J, Pompano RR, Santiago FW, et al. The use of self-adjuvanting nanofiber vaccines to elicit high-affinity B cell responses to peptide antigens without inflammation. Biomaterials. 2013;34(34):8776-8785.

Cho, H.-J.; Kim, J.-Y.; Lee, Y.; Kim, J. M.; Kim, Y. B.; Chun, T.; Oh, Y.-K., Enhanced humoral and cellular immune responses after sublingual immunization against human papillomavirus 16 L1 protein with adjuvants. Vaccine 2010, 28 (14), 2598-2606.

Elliott SL, Suhrbier A, Miles JJ, et al. Phase I Trial of a CD8+ T-Cell Peptide Epitope-Based Vaccine for Infectious Mononucleosis. JVI. 2008;82(3):1448-1457.

Fremont DH, Hendrickson WA, Marrack P, Kappler J. Structures of an MHC Class II molecule with covalently bound single peptides. Science. 1996;272(5264).

Galazka et al. Thermostabilily of Vaccines. World Health Organization, 1998, p. 1-64 [online].

Gasiorowski JZ, Collier JH. Directed Intermixing in Multicomponent Self-Assembling Biomaterials. Biomacromolecules. 2011;12(10):3549-3558. doi:10.1021/bm200763y.

Grandi A, Fantappiè L, Irene C, et al. Vaccination With a FAT1-Derived B Cell Epitope Combined With Tumor-Specific B and T Cell Epitopes Elicits Additive Protection in Cancer Mouse Models. Front Oncol. 2018;8:207-214.

Bachmann MF et al. The Influence of Antigen Organization on B Cell Responsiveness. Science. 1993;262(5138):1448-1451.

Hudalla GA, Sun T, Gasiorowski JZ, Han H, Tian YF, Chong AS, Collier JH. Gradated assembly of multiple proteins into supramolecular nanomaterials. Nat Mater. Aug. 2014;13(8):829-36.

Hurtgen BJ, Hung C-Y, Ostroff GR, Levitz SM, Cole GT. Construction and Evaluation of a Novel Recombinant T Cell Epitope-Based Vaccine against Coccidioidomycosis. Deepe GS Jr., ed. Infect Immun. 2012;80(11):3960-3974.

International Search Report and Written Opinion for International Patent Application No. PCT/US2020/031351, dated Oct. 13, 2020.

International Search Report and Written Opinion for International Patent Application No. PCT/US2020/053095, dated Feb. 25, 2021.

Jin X, Newman MJ, De-Rosa S, et al. A novel HIV T helper epitope-based vaccine elicits cytokine-secreting HIV-specific CD4+ T cells in a Phase I clinical trial in HIV-uninfected adults. Vaccine. 2009;27(50):7080-7086.

Kelly SH, Shores LS, Votaw NL, Collier JH. Biomaterial strategies for generating therapeutic immune responses. Adv Drug Deliv Rev. May 15, 2017;114:3-18.

Kelly, S. H.; Wu, Y.; Varadhan, A. K.; Curvino, E. J.; Chong, A. S.; Collier, J. H., Enabling sublingual peptide immunization with molecular self-assemblies. Biomaterials 2020, 119903.

Khutoryanskiy VV. Beyond PEGylation: Alternative surface-modification of nanoparticles with mucus-inert biomaterials. Advanced Drug Delivery Reviews 124:140-149, 2018.

Kraan, H.; Vrieling, H.; Czerkinsky, C.; Jiskoot, W.; Kersten, G.; Amorij, J.-P., Buccal and sublingual vaccine delivery. Journal of controlled release 2014, 190, 580-592.

Lagerlof F, Dawes C. The Volume of Saliva in the Mouth Before and After Swallowing. Journal of Dental Research. 1984;63(5):618-621.

Li H-B, Zhang J-Y, He Y-F, et al. Systemic immunization with an epitope-based vaccine elicits a Th1-biased response and provides protection against Helicobacter pylori in mice. Vaccine. 2012;31(1):120-126.

Mahdavi M, Moreau V, Kheirollahi M. Identification of B and T cell epitope based peptide vaccine from IGF-1 receptor in breast cancer. Journal of Molecular Graphics and Modelling. 2017;75:316-321.

Mora-Solano C, Wen Y, Han H, et al. Active immunotherapy for TNF-mediated inflammation using self-assembled peptide nanofibers. Biomaterials. 2017; 149:1-11.

Mountford AP, Fisher A, Wilson RA. The profile of IgG1 and IgG2a antibody responses in mice exposed to Schistosoma mansoni. Parasite Immunology. 1994;16:521-527.

Moutaftsi M, Bui H-H, Peters B, et al. Vaccinia virus-specific CD4+ T cell responses target a set of antigens largely distinct from those targeted by CD8+ T cell responses. The Journal of Immunology. 2007; 178(11):6814-6820.

Neuhaus O, Farina C, Yassouridis A, et al. Multiple sclerosis: Comparison of copolymer-1- reactive T cell lines from treated and untreated subjects reveals cytokine shift from T helper 1 to T helper 2 cells. Proc Natl Acad Sci USA. 2000;97(13):7452-7457.

Oany A, Pervin T, Emran A. Design of an epitope-based peptide vaccine against spike protein of human coronavirus: an in silico approach. DDDT. Aug. 2014:1139-11.

Ohagan DT, MacKichan ML, Singh M. Recent developments in adjuvants for vaccines against infectious diseases. Biomolecular Engineering. 2001;18:69-75.

Ohtake, S.; Wang, Y. J., Trehalose: current use and future applications. Journal of pharmaceutical sciences 2011, 100 (6), 2020-2053.

Olsen, A.W..; Hansen, P. R.; Holm, A.; Andersen, P., Efficient protection against *Mycobacterium tuberculosis* by vaccination with a single subdominant epitope from the ESAT-6 antigen. European journal of immunology 2000, 30 (6), 1724-1732.

Onodi F, Maherzi-Mechalikh C, Mougel A, et al. High Therapeutic Efficacy of a New Survivin LSP-Cancer Vaccine Containing CD4+ and CD8+ T-Cell Epitopes. Front Oncol. 2018;8:517.

Pompano RR, Chen J, Verbus EA, et al. Titrating T-Cell Epitopes within Self-Assembled Vaccines Optimizes CD4+ Helper T Cell and Antibody Outputs. Adv Healthcare Mater. 2014;3(11):1898-1908.

Rudra JS, Tian YF, Jung JP, Collier JH. A self-assembling peptide acting as an immune adjuvant. Proc Natl Acad Sci USA. 2010;107(2):622-627.

Rudra, J. S.; Sun, T.; Bird, K. C.; Daniels, M. D.; Gasiorowski, J. Z.; Chong, A. S.; Collier, J. H., Modulating adaptive immune responses to peptide self-assemblies. Acs Nano 2012, 6 (2), 1557-1564.

Sastry, S. V.; Nyshadham, J. R .; Fix, J. A., Recent technological advances in oral drug delivery—a review. Pharmaceutical science & technology today 2000, 3 (4), 138-145.

Seroski and Hudalia , Self-Assembled Peptide and Protein Nanofibers for Biomedical Applications, Chapter 19 In Biomedical Applications of Functionalized Nanomaterials, (2018) 569-598.

Sloan-Lancaster J, Allen PM. Altered peptide ligand-induced partial T cell activation: molecular mechanisms and role in T cell biology. Annu Rev Immunol. 1996; 14:1-27.

Sohaebuddin SK, Thevenot PT, Baker D, Eaton JW, Tang L. Nanomaterial cytotoxicity is composition, size, and cell type dependent. Particle and Fibre Toxicology. 2010;7(22).

Sun, T.; Han, H.; Hudalla, G. A.; Wen, Y.; Pompano, R. R.; Collier, J. H., Thermal stability of self-assembled peptide vaccine materials. Acta biomaterialia 2016, 30, 62-71.

Teitelbaum D, Meshorer A, Hirshfeld T, Arnon R, Sela M. Suppression of experimental allergic encephalomyelitis by a synthetic polypeptide. Eur J Immunol. 1971;1(4):242-248.

Turecek PL, Bossard MJ, Schoetens F, Ivens IA. PEGylation of Biopharmaceuticals: A Review of Chemistry and Nonclinical Safety Information of Approved Drugs. J Pharm Sci. Feb. 2016;105(2):460-475.

Van Damme, P.; Cramm, M.; Safary, A.; Vandepapeliere, P.; Meheus, A., Heat stability of a recombinant DNA hepatitis B vaccine. Vaccine 1992, 10 (6), 366-367.

Weber MS, Prod'homme T, Youssef S, et al. Type II monocytes modulate T cell-mediated central nervous system autoimmune disease. Nat Med. 2007; 13(8):935-943.

Wen, Y.; Collier, J. H., Supramolecular peptide vaccines: tuning adaptive immunity. Current opinion in immunology 2015, 35, 73-79.

Wilkhu et al. Development of a solid dosage platform for the oral delivery of bilayer vesicles. Eur J Pharm Sci. Oct. 15, 2017;108:71-77.

Wu, Y.; Norberg, P. K.; Reap, E. A.; Congdon, K. L.; Fries, C. N.; Kelly, S. H.; Sampson, J. H.; Conticello, V. P.; Collier, J. H., A Supramolecular Vaccine Platform Based on a-Helical Peptide Nanofibers. ACS Biomaterials Science & Engineering 2017, 3 (12), 3128-3132.

(56) References Cited

OTHER PUBLICATIONS

Xu H, Hu C, Gong R, et al. Evaluation of a Novel Chimeric B Cell Epitope-Based Vaccine against Mastitis Induced by Either *Streptococcus agalactiae* or *Staphylococcus aureus* in Mice. Clin Vaccine Immunol. 2011; 18(6):893-900.

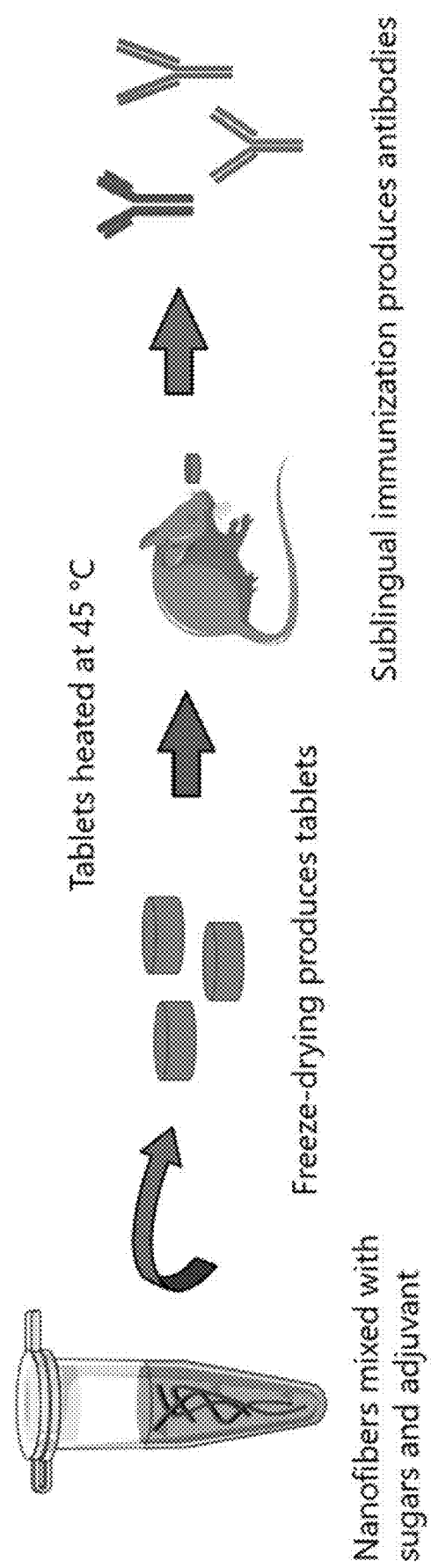

```
                           SEQUENCE LISTING

<160> NUMBER OF SEQ ID NOS: 93

<210> SEQ ID NO 1
<211> LENGTH: 11
<212> TYPE: PRT
<213> ORGANISM: Artificial Sequence
<220> FEATURE:
<223> OTHER INFORMATION: Synthetic- Q11 self-assembling polypeptide

<400> SEQUENCE: 1

Gln Gln Lys Phe Gln Phe Gln Phe Glu Gln Gln
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic- self-assembling polypeptide

<400> SEQUENCE: 2

Trp Gln Gln Lys Phe Gln Phe Gln Phe Glu Gln Gln
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 3

Ala Glu Ala Lys Ala Glu Ala Lys Ala Glu Ala Lys Ala Glu Ala Lys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 4

Ala Glu Ala Glu Ala Lys Ala Lys Ala Glu Ala Glu Ala Lys Ala Lys
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 5

Ala Glu Ala Glu Ala Glu Ala Glu Ala Lys Lys Glu Ala Lys Lys Glu
1               5                   10                  15

<210> SEQ ID NO 6
<211> LENGTH: 8
<212> TYPE: PRT
<213> ORGANISM: Artificial Sequence
```

```
<220> FEATURE:
<223> OTHER INFORMATION: Synthetic- self-assembling polypeptide

<400> SEQUENCE: 6

Met Glu Met Glu Met Lys Met Lys
1               5

<210> SEQ ID NO 7
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 7

Arg Ala Asp Ala Arg Ala Asp Ala Arg Ala Asp Ala Arg Ala Asp Ala
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 8

Arg Ala Arg Ala Arg Asp Arg Asp Arg Ala Arg Ala Arg Asp Arg Asp
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 9

Arg Ala Arg Ala Arg Ala Arg Ala Arg Asp Arg Asp Arg Asp Arg Asp
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 10

Ala Asp Ala Asp Ala Asp Ala Asp Ala Arg Ala Arg Ala Arg Ala Arg
1               5                   10                  15

<210> SEQ ID NO 11
<211> LENGTH: 4
<212> TYPE: PRT
<213> ORGANISM: Artificial Sequence
<220> FEATURE:
<223> OTHER INFORMATION: Synthetic- self-assembling polypeptide

<400> SEQUENCE: 11

Lys Leu Asp Leu
1

<210> SEQ ID NO 12
<211> LENGTH: 8
<212> TYPE: PRT
<213> ORGANISM: Artificial Sequence
<220> FEATURE:
```

<223> OTHER INFORMATION: Synthetic- self-assembling polypeptide

<400> SEQUENCE: 12

Phe Lys Phe Glu Phe Lys Phe Glu
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic- self-assembling polypeptide

<400> SEQUENCE: 13

Phe Lys Phe Glu
1

<210> SEQ ID NO 14
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 14

Phe Glu Phe Glu Phe Lys Phe Lys Phe Glu Phe Glu Phe Lys Phe Lys
1               5                   10                  15

<210> SEQ ID NO 15
<211> LENGTH: 20
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 15

Val Lys Val Lys Val Lys Val Lys Val Pro Pro Thr Lys Val Lys Val
1               5                   10                  15

Lys Val Lys Val
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 16

Val Lys Val Lys Val Lys Val Lys Val Pro Pro Thr Lys Val Lys Thr
1               5                   10                  15

Lys Val Lys Val
            20

<210> SEQ ID NO 17
<211> LENGTH: 20
<212> TYPE: PRT
<213> ORGANISM: Artificial Sequence
<220> FEATURE:

```
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 17

Val Lys Val Lys Val Lys Thr Lys Val Pro Pro Thr Lys Val Lys Thr
1               5                   10                  15

Lys Val Lys Val
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: K is D-lysine

<400> SEQUENCE: 18

Lys Val Lys Val Lys Val Lys Val Lys Pro Pro Ser Val Lys Val Lys
1               5                   10                  15

Val Lys Val Lys
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 19

Val Lys Val Lys Val Lys Val Lys Val Pro Pro Ser Lys Val Lys Val
1               5                   10                  15

Lys Val Lys Val
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 20

Val Lys Val Lys Val Lys Val Lys Val Pro Pro Thr Lys Val Lys Glu
1               5                   10                  15

Lys Val Lys Val
            20

<210> SEQ ID NO 21
<211> LENGTH: 20
<212> TYPE: PRT
<213> ORGANISM: Artificial Sequence
```

```
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 21

Val Lys Val Lys Val Lys Val Lys Val Pro Pro Thr Lys Val Lys Cys
1               5                   10                  15

Lys Val Lys Val
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 22

Val Lys Val Lys Val Lys Val Lys Val Pro Pro Thr Lys Val Glu Val
1               5                   10                  15

Lys Val Lys Val
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 23

Val Glu Val Lys Val Lys Val Lys Val Pro Pro Thr Lys Val Lys Val
1               5                   10                  15

Lys Val Lys Val
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 24

Val Lys Val Glu Val Lys Val Lys Val Pro Pro Thr Lys Val Lys Val
1               5                   10                  15

Lys Val Lys Val
            20

<210> SEQ ID NO 25
<211> LENGTH: 20
<212> TYPE: PRT
```

```
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 25

Val Lys Val Lys Val Glu Val Lys Val Pro Pro Thr Lys Val Lys Val
1               5                   10                  15

Lys Val Lys Val
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 26

Val Lys Val Lys Val Lys Val Glu Val Pro Pro Thr Lys Val Lys Val
1               5                   10                  15

Lys Val Lys Val
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 27

Val Lys Val Lys Val Lys Val Lys Val Pro Pro Thr Glu Val Lys Val
1               5                   10                  15

Lys Val Lys Val
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (9)..(9)
<223> OTHER INFORMATION: V is D-valine

<400> SEQUENCE: 28

Val Lys Val Lys Val Lys Val Lys Val Pro Pro Thr Lys Val Lys Val
1               5                   10                  15

Glu Val Lys Val
            20

<210> SEQ ID NO 29
<211> LENGTH: 11
```

```
<212> TYPE: PRT
<213> ORGANISM: Artificial Sequence
<220> FEATURE:
<223> OTHER INFORMATION: Synthetic- self-assembling polypeptide

<400> SEQUENCE: 29

Gln Gln Arg Gln Gln Gln Gln Gln Glu Gln Gln
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic- self-assembling polypeptide

<400> SEQUENCE: 30

Gln Gln Arg Phe Gln Trp Gln Phe Glu Gln Gln
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic- self-assembling polypeptide

<400> SEQUENCE: 31

Gln Gln Arg Phe Gln Trp Gln Phe Gln Gln Gln
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic- self-assembling polypeptide

<400> SEQUENCE: 32

Gln Gln Arg Phe Glu Trp Glu Phe Glu Gln Gln
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (3)..(3)
<223> OTHER INFORMATION: Xaa is ornithine
<220> FEATURE:
<221> NAME/KEY: MISC_FEATURE
<222> LOCATION: (5)..(5)
<223> OTHER INFORMATION: Xaa is ornithine
<220> FEATURE:
<221> NAME/KEY: MISC_FEATURE
<222> LOCATION: (7)..(7)
<223> OTHER INFORMATION: Xaa is ornithine

<400> SEQUENCE: 33

Gln Gln Xaa Phe Xaa Trp Xaa Phe Gln Gln Gln
1               5                   10

<210> SEQ ID NO 34
<211> LENGTH: 11
<212> TYPE: PRT
<213> ORGANISM: Artificial Sequence
```

```
<220> FEATURE:
<223> OTHER INFORMATION: Synthetic- self-assembling polypeptide

<400> SEQUENCE: 34

Ser Ser Arg Phe Ser Trp Ser Phe Glu Ser Ser
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (7)..(7)
<223> OTHER INFORMATION: Xaa is ornithine

<400> SEQUENCE: 35

Gln Gln Arg Phe Xaa Trp Xaa Phe Glu Gln Gln
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic- self-assembling polypeptide

<400> SEQUENCE: 36

Ser Ser Arg Phe Glu Trp Glu Phe Glu Ser Ser
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (5)..(5)
<223> OTHER INFORMATION: Xaa is ornithine
<220> FEATURE:
<221> NAME/KEY: MISC_FEATURE
<222> LOCATION: (7)..(7)
<223> OTHER INFORMATION: Xaa is ornithine

<400> SEQUENCE: 37

Ser Ser Arg Phe Xaa Trp Xaa Phe Glu Ser Ser
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (5)..(5)
<223> OTHER INFORMATION: Xaa is ornithine
<220> FEATURE:
<221> NAME/KEY: MISC_FEATURE
<222> LOCATION: (5)..(5)
<223> OTHER INFORMATION: Xaa is ornithine
<220> FEATURE:
```

```
<221> NAME/KEY: MISC_FEATURE
<222> LOCATION: (7)..(7)
<223> OTHER INFORMATION: Xaa is ornithine

<400> SEQUENCE: 38

Asn Asn Arg Phe Xaa Trp Xaa Phe Glu Gln Gln
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (5)..(5)
<223> OTHER INFORMATION: Xaa is ornithine
<220> FEATURE:
<221> NAME/KEY: MISC_FEATURE
<222> LOCATION: (7)..(7)
<223> OTHER INFORMATION: Xaa is ornithine

<400> SEQUENCE: 39

Thr Thr Arg Phe Xaa Trp Xaa Phe Glu Thr Thr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (5)..(5)
<223> OTHER INFORMATION: Xaa is ornithine
<220> FEATURE:
<221> NAME/KEY: MISC_FEATURE
<222> LOCATION: (7)..(7)
<223> OTHER INFORMATION: Xaa is ornithine

<400> SEQUENCE: 40

Gln Gln Arg Gln Xaa Gln Xaa Gln Glu Gln Gln
1               5                   10

<210> SEQ ID NO 41
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 41

Phe Glu Phe Glu Phe Lys Phe Lys Phe Glu Phe Glu Phe Lys Phe Lys
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 42

Phe Glu Phe Glu Ala Lys Phe Lys Phe Glu Phe Glu Phe Lys Phe Lys
1               5                   10                  15

<210> SEQ ID NO 43
```

```
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 43

Phe Glu Phe Glu Phe Lys Leu Lys Ile Glu Phe Glu Phe Lys Phe Lys
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 44

Phe Glu Ala Glu Val Lys Leu Lys Leu Glu Leu Glu Val Lys Phe Lys
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 45

Gly Glu Ala Glu Val Lys Leu Lys Ile Glu Leu Glu Val Lys Ala Lys
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 46

Gly Glu Ala Glu Val Lys Ile Lys Ile Glu Val Glu Ala Lys Gly Lys
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 47

Ile Glu Val Glu Ala Lys Gly Lys Gly Glu Ala Glu Val Lys Ile Lys
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic- self-assembling polypeptide

<400> SEQUENCE: 48

Ile Glu Leu Glu Val Lys Ala Lys Gly Glu Ala Glu Lys Leu Lys
1               5                   10                  15

<210> SEQ ID NO 49
<211> LENGTH: 16
```

<212> TYPE: PRT
<213> ORGANISM: Artificial Sequence
<220> FEATURE:
<223> OTHER INFORMATION: Synthetic- self-assembling polypeptide

<400> SEQUENCE: 49

Ile Glu Leu Glu Val Lys Ala Lys Ala Glu Ala Glu Val Lys Leu Lys
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 50

Ile Glu Ala Glu Gly Lys Gly Lys Ile Glu Gly Glu Ala Lys Ile Lys
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 51

Lys Lys Gln Leu Gln Leu Gln Leu Gln Leu Gln Leu Gln Leu Lys Lys
1               5                   10                  15

<210> SEQ ID NO 52
<211> LENGTH: 14
<212> TYPE: PRT
<213> ORGANISM: Artificial Sequence
<220> FEATURE:
<223> OTHER INFORMATION: Synthetic- self-assembling polypeptide

<400> SEQUENCE: 52

Glu Gln Leu Gln Leu Gln Leu Gln Leu Gln Leu Gln Leu Glu
1               5                   10

<210> SEQ ID NO 53
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 53

Lys Lys Ser Leu Ser Leu Ser Leu Ser Leu Ser Leu Ser Leu Lys Lys
1               5                   10                  15

<210> SEQ ID NO 54
<211> LENGTH: 14
<212> TYPE: PRT
<213> ORGANISM: Artificial Sequence
<220> FEATURE:
<223> OTHER INFORMATION: Synthetic- self-assembling polypeptide

<400> SEQUENCE: 54

Glu Ser Leu Ser Leu Ser Leu Ser Leu Ser Leu Ser Leu Glu
1               5                   10

<210> SEQ ID NO 55
<211> LENGTH: 14
<212> TYPE: PRT

```
<213> ORGANISM: Artificial Sequence
<220> FEATURE:
<223> OTHER INFORMATION: Synthetic- self-assembling polypeptide

<400> SEQUENCE: 55

Glu Cys Leu Ser Leu Cys Leu Ser Leu Cys Leu Ser Leu Glu
1               5                   10

<210> SEQ ID NO 56
<211> LENGTH: 6
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (4)..(4)
<223> OTHER INFORMATION: X is Q, S, N, G, L, or norvaline

<400> SEQUENCE: 56

Ile Ile Ile Xaa Gly Lys
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic- self-assembling polypeptide

<400> SEQUENCE: 57

Phe Lys Phe Glu Phe Lys Phe Glu
1               5

<210> SEQ ID NO 58
<211> LENGTH: 21
<212> TYPE: PRT
<213> ORGANISM: Artificial Sequence
<220> FEATURE:
<223> OTHER INFORMATION: Synthetic- self-assembling polypeptide

<400> SEQUENCE: 58

Lys Ser Leu Ser Leu Ser Leu Arg Gly Ser Leu Ser Leu Ser Leu Lys
1               5                   10                  15

Gly Arg Gly Asp Ser
            20

<210> SEQ ID NO 59
<211> LENGTH: 14
<212> TYPE: PRT
<213> ORGANISM: Artificial Sequence
<220> FEATURE:
<223> OTHER INFORMATION: Synthetic- self-assembling polypeptide

<400> SEQUENCE: 59

Lys Lys Ser Leu Ser Leu Ser Ala Ser Leu Ser Leu Lys Lys
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic- self-assembling polypeptide

<400> SEQUENCE: 60

Gln Gln Lys Phe Lys Phe Lys Phe Lys Gln Gln
```

<210> SEQ ID NO 61
<211> LENGTH: 11
<212> TYPE: PRT
<213> ORGANISM: Artificial Sequence
<220> FEATURE:
<223> OTHER INFORMATION: Synthetic- self-assembling polypeptide

<400> SEQUENCE: 61

Glu Gln Glu Phe Glu Phe Glu Phe Glu Gln Glu
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic- self-assembling polypeptide

<400> SEQUENCE: 62

Gln Gln Lys Phe Gln Phe Gln Phe Glu Gln Glu Gln Gln
1               5                   10

<210> SEQ ID NO 63
<211> LENGTH: 29
<212> TYPE: PRT
<213> ORGANISM: Artificial Sequence
<220> FEATURE:
<223> OTHER INFORMATION: Synthetic- self-assembling polypeptide

<400> SEQUENCE: 63

Gln Ala Arg Ile Leu Glu Ala Asp Ala Glu Ile Leu Arg Ala Tyr Ala
1               5                   10                  15

Arg Ile Leu Glu Ala His Ala Glu Ile Leu Arg Ala Gln
            20                  25

<210> SEQ ID NO 64
<211> LENGTH: 13
<212> TYPE: PRT
<213> ORGANISM: Artificial Sequence
<220> FEATURE:
<223> OTHER INFORMATION: Synthetic- self-assembling polypeptide

<400> SEQUENCE: 64

Ala Ala Ala Ala Gly Gly Gly Glu Ile Lys Val Ala Val
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Synthetic- self-assembling polypeptide
<220> FEATURE:
<221> NAME/KEY: MISC_FEATURE
<222> LOCATION: (8)..(8)
<223> OTHER INFORMATION: X is phosphoserine

<400> SEQUENCE: 65

Cys Cys Cys Cys Gly Gly Gly Xaa Gly Gly Gly Arg Gly Asp
1               5                   10

<210> SEQ ID NO 66
<211> LENGTH: 29
<212> TYPE: PRT
<213> ORGANISM: Artificial Sequence

```
<220> FEATURE:
<223> OTHER INFORMATION: Synthetic- self-assembling polypeptide

<400> SEQUENCE: 66

Gln Ala Lys Ile Leu Glu Ala Asp Ala Glu Ile Leu Lys Ala Tyr Ala
1               5                   10                  15
Lys Ile Leu Glu Ala His Ala Glu Ile Leu Lys Ala Gln
            20                  25

<210> SEQ ID NO 67
<211> LENGTH: 23
<212> TYPE: PRT
<213> ORGANISM: Artificial Sequence
<220> FEATURE:
<223> OTHER INFORMATION: Synthetic- self-assembling polypeptide

<400> SEQUENCE: 67

Ala Asp Ala Glu Ile Leu Arg Ala Tyr Ala Arg Ile Leu Glu Ala His
1               5                   10                  15
Ala Glu Ile Leu Arg Ala Gln
            20

<210> SEQ ID NO 68
<211> LENGTH: 4
<212> TYPE: PRT
<213> ORGANISM: Artificial Sequence
<220> FEATURE:
<223> OTHER INFORMATION: Synthetic- peptide linker

<400> SEQUENCE: 68

Ser Gly Ser Gly
1

<210> SEQ ID NO 69
<211> LENGTH: 4
<212> TYPE: PRT
<213> ORGANISM: Artificial Sequence
<220> FEATURE:
<223> OTHER INFORMATION: Synthetic- peptide linker

<400> SEQUENCE: 69

Gly Ser Gly Ser
1

<210> SEQ ID NO 70
<211> LENGTH: 4
<212> TYPE: PRT
<213> ORGANISM: Artificial Sequence
<220> FEATURE:
<223> OTHER INFORMATION: Synthetic- peptide linker

<400> SEQUENCE: 70

Ser Ser Ser Ser
1

<210> SEQ ID NO 71
<211> LENGTH: 4
<212> TYPE: PRT
<213> ORGANISM: Artificial Sequence
<220> FEATURE:
<223> OTHER INFORMATION: Synthetic- peptide linker

<400> SEQUENCE: 71

Gly Gly Gly Ser
1
```

<210> SEQ ID NO 72
<211> LENGTH: 5
<212> TYPE: PRT
<213> ORGANISM: Artificial Sequence
<220> FEATURE:
<223> OTHER INFORMATION: Synthetic- peptide linker

<400> SEQUENCE: 72

Gly Gly Ala Ala Tyr
1               5

<210> SEQ ID NO 73
<211> LENGTH: 20
<212> TYPE: PRT
<213> ORGANISM: Artificial Sequence
<220> FEATURE:
<223> OTHER INFORMATION: Synthetic- PAS peptide

<400> SEQUENCE: 73

Ala Ala Pro Ala Ser Pro Ala Pro Ala Ala Pro Ser Ala Pro Ala Pro
1               5                   10                  15

Ala Ala Pro Ser
            20

<210> SEQ ID NO 74
<211> LENGTH: 20
<212> TYPE: PRT
<213> ORGANISM: Artificial Sequence
<220> FEATURE:
<223> OTHER INFORMATION: Synthetic- PAS peptide

<400> SEQUENCE: 74

Ala Pro Ser Ser Pro Ser Pro Ser Ala Pro Ser Ser Pro Ser Pro Ala
1               5                   10                  15

Ser Pro Ser Ser
            20

<210> SEQ ID NO 75
<211> LENGTH: 19
<212> TYPE: PRT
<213> ORGANISM: Artificial Sequence
<220> FEATURE:
<223> OTHER INFORMATION: Synthetic- PAS peptide

<400> SEQUENCE: 75

Ala Pro Ser Ser Pro Ser Pro Ser Ala Pro Ser Ser Pro Ser Pro Ala
1               5                   10                  15

Ser Pro Ser

<210> SEQ ID NO 76
<211> LENGTH: 20
<212> TYPE: PRT
<213> ORGANISM: Artificial Sequence
<220> FEATURE:
<223> OTHER INFORMATION: Synthetic- PAS peptide

<400> SEQUENCE: 76

Ser Ser Pro Ser Ala Pro Ser Pro Ser Ser Pro Ala Ser Pro Ser Pro
1               5                   10                  15

Ser Ser Pro Ala
            20

<210> SEQ ID NO 77
<211> LENGTH: 24

```
<212> TYPE: PRT
<213> ORGANISM: Artificial Sequence
<220> FEATURE:
<223> OTHER INFORMATION: Synthetic- PAS peptide

<400> SEQUENCE: 77

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 78
<211> LENGTH: 20
<212> TYPE: PRT
<213> ORGANISM: Artificial Sequence
<220> FEATURE:
<223> OTHER INFORMATION: Synthetic- PAS peptide

<400> SEQUENCE: 78

Ala Ser Ala Ala Ala Pro Ala Ala Ala Ser Ala Ala Ala Ser Ala Pro
1               5                   10                  15

Ser Ala Ala Ala
            20

<210> SEQ ID NO 79
<211> LENGTH: 20
<212> TYPE: PRT
<213> ORGANISM: Artificial Sequence
<220> FEATURE:
<223> OTHER INFORMATION: Synthetic- PAS peptide

<400> SEQUENCE: 79

Ala Ser Pro Ala Ala Pro Ala Pro Ala Ser Pro Ala Ala Pro Ala Pro
1               5                   10                  15

Ser Ala Pro Ala
            20

<210> SEQ ID NO 80
<211> LENGTH: 16
<212> TYPE: PRT
<213> ORGANISM: Artificial Sequence
<220> FEATURE:
<223> OTHER INFORMATION: Synthetic- self-assembling polypeptide

<400> SEQUENCE: 80

Lys Lys Ser Leu Ser Leu Ser Ala Ser Ala Ser Leu Ser Leu Lys Lys
1               5                   10                  15

<210> SEQ ID NO 81
<211> LENGTH: 32
<212> TYPE: PRT
<213> ORGANISM: Artificial Sequence
<220> FEATURE:
<223> OTHER INFORMATION: Synthetic- OVAQ11 polypeptide

<400> SEQUENCE: 81

Ile Ser Gln Ala Val His Ala Ala His Ala Glu Ile Asn Glu Ala Gly
1               5                   10                  15

Arg Ser Gly Ser Gly Gln Gln Lys Phe Gln Phe Gln Phe Glu Gln Gln
            20                  25                  30

<210> SEQ ID NO 82
<211> LENGTH: 17
<212> TYPE: PRT
<213> ORGANISM: Artificial Sequence
```

```
<220> FEATURE:
<223> OTHER INFORMATION: Synthetic- pOVA polypeptide

<400> SEQUENCE: 82

Ile Ser Gln Ala Val His Ala Ala His Ala Glu Ile Asn Glu Ala Gly
1               5                   10                  15

Arg

<210> SEQ ID NO 83
<211> LENGTH: 21
<212> TYPE: PRT
<213> ORGANISM: Artificial Sequence
<220> FEATURE:
<223> OTHER INFORMATION: Synthetic- C-ESAT6 polypeptide

<400> SEQUENCE: 83

Cys Tyr Gln Gly Val Gln Gln Lys Trp Asp Ala Thr Ala Thr Glu Leu
1               5                   10                  15

Asn Asn Ala Leu Gln
            20

<210> SEQ ID NO 84
<211> LENGTH: 40
<212> TYPE: PRT
<213> ORGANISM: Artificial Sequence
<220> FEATURE:
<223> OTHER INFORMATION: Synthetic- Q11ESAT6 polypeptide

<400> SEQUENCE: 84

Ser Gly Ser Gly Gln Gln Lys Phe Gln Phe Gln Phe Glu Gln Gln Ser
1               5                   10                  15

Gly Ser Gly Cys Tyr Gln Gly Val Gln Gln Lys Trp Asp Ala Thr Ala
            20                  25                  30

Thr Glu Leu Asn Asn Ala Leu Gln
        35                  40

<210> SEQ ID NO 85
<211> LENGTH: 49
<212> TYPE: PRT
<213> ORGANISM: Artificial Sequence
<220> FEATURE:
<223> OTHER INFORMATION: Synthetic- Q11PepIroN polypeptide

<400> SEQUENCE: 85

Ser Gly Ser Gly Gln Gln Lys Phe Gln Phe Gln Phe Glu Gln Gln Ser
1               5                   10                  15

Gly Ser Gly Tyr Leu Leu Tyr Ser Lys Gly Asn Gly Cys Pro Lys Asp
            20                  25                  30

Ile Thr Ser Gly Gly Cys Tyr Leu Ile Gly Asn Lys Asp Leu Asp Pro
        35                  40                  45

Glu

<210> SEQ ID NO 86
<211> LENGTH: 48
<212> TYPE: PRT
<213> ORGANISM: Artificial Sequence
<220> FEATURE:
<223> OTHER INFORMATION: Synthetic- Q11PepIutA polypeptide

<400> SEQUENCE: 86

Ser Gly Ser Gly Gln Gln Lys Phe Gln Phe Gln Phe Glu Gln Gln Ser
1               5                   10                  15
```

-continued

Gly Ser Gly Val Asp Asp Ile Asp Tyr Thr Gln Gln Gln Lys Ile Ala
            20                  25                  30

Ala Gly Lys Ala Ile Ser Ala Asp Ala Ile Pro Gly Gly Ser Val Asp
        35                  40                  45

<210> SEQ ID NO 87
<211> LENGTH: 51
<212> TYPE: PRT
<213> ORGANISM: Artificial Sequence
<220> FEATURE:
<223> OTHER INFORMATION: Synthetic- Q11PepIreA polypeptide

<400> SEQUENCE: 87

Ser Gly Ser Gly Gln Gln Lys Phe Gln Phe Gln Phe Glu Gln Gln Ser
1               5                   10                  15

Gly Ser Gly Gly Ile Ala Lys Ala Phe Arg Ala Pro Ser Ile Arg Glu
            20                  25                  30

Val Ser Pro Gly Phe Gly Thr Leu Thr Gln Gly Gly Ala Ser Ile Met
        35                  40                  45

Tyr Gly Asn
    50

<210> SEQ ID NO 88
<211> LENGTH: 30
<212> TYPE: PRT
<213> ORGANISM: Artificial Sequence
<220> FEATURE:
<223> OTHER INFORMATION: Synthetic- VACQ11 polypeptide

<400> SEQUENCE: 88

Gln Leu Val Phe Asn Ser Ile Ser Ala Arg Ala Leu Lys Ala Tyr Ser
1               5                   10                  15

Gly Ser Gly Gln Gln Lys Phe Gln Phe Gln Phe Glu Gln Gln
            20                  25                  30

<210> SEQ ID NO 89
<211> LENGTH: 5
<212> TYPE: PRT
<213> ORGANISM: Artificial Sequence
<220> FEATURE:
<223> OTHER INFORMATION: Synthetic- generic ZIPP peptide
<220> FEATURE:
<221> NAME/KEY: MISC_FEATURE
<222> LOCATION: (3)..(3)
<223> OTHER INFORMATION: Xaa is a cationic amino acid
<220> FEATURE:
<221> NAME/KEY: MISC_FEATURE
<222> LOCATION: (4)..(4)
<223> OTHER INFORMATION: Xaa is an anionic amino acid

<400> SEQUENCE: 89

Val Pro Xaa Xaa Gly
1               5

<210> SEQ ID NO 90
<211> LENGTH: 5
<212> TYPE: PRT
<213> ORGANISM: Artificial Sequence
<220> FEATURE:
<223> OTHER INFORMATION: Synthetic- ZIPP peptide

<400> SEQUENCE: 90

Val Pro Lys Glu Gly
1               5

```
<210> SEQ ID NO 91
<211> LENGTH: 5
<212> TYPE: PRT
<213> ORGANISM: Artificial Sequence
<220> FEATURE:
<223> OTHER INFORMATION: Synthetic- ZIPP peptide

<400> SEQUENCE: 91

Val Pro Arg Glu Gly
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic- ZIPP peptide

<400> SEQUENCE: 92

Val Pro Lys Asp Gly
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic- ZIPP peptide

<400> SEQUENCE: 93

Val Pro Arg Asp Gly
1               5
```

TABLETIZATION OF PEPTIDE SELF-ASSEMBLIES AND METHODS OF MAKING AND USING THE SAME

CROSS-REFERENCE TO RELATED APPLICATIONS

This patent application is a national stage filing under 35 U.S.C. § 371 of International Patent Application No. PCT/US2020/053095, filed Sep. 28, 2020, which claims the benefit of priority of U.S. Provisional Application No. 62/906,893 filed on Sep. 27, 2019, the contents of which are incorporated by reference in their entirety.

STATEMENT REGARDING FEDERALLY SPONSORED RESEARCH

This invention was made with Government support under grant number NIBIB 5R01EB009701 and NIAID 5R01AI118182 awarded by the National Institutes of Health and under grant number DGE-1644868 awarded by the National Science Foundation Graduate Research Fellowship Program. The Federal Government has certain rights to this invention.

SEQUENCE LISTING

A Sequence Listing accompanies this application and is submitted as an ASCII text file of the sequence listing named "155554_00554_ST25.txt" which is 27.1 KB in size and was created on Sep. 28, 2020. The sequence listing is electronically submitted via EFS-Web with the application and is incorporated herein by reference in its entirety.

BACKGROUND

Global vaccination coverage against infectious diseases in lower- and middle-income countries still lags behind higher-income countries, resulting in preventable deaths.[1] Improving global vaccine coverage is a complex and multifaceted challenge, a major component of which is the chain of distribution.[2] Vaccines must be transported and stored within a continuous cold-chain near 4° C. to prevent loss of potency,[3] but poorly maintained equipment and unreliable electricity grids in lower- and middle-income countries make such transport difficult.[2] Inequities of distribution occur even within countries due to transportation costs and proximity to health care facilities where trained personnel can safely administer the vaccines.[4] To address these challenges, heat-stable and self-deliverable vaccines are needed.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure is based, in part, on the findings by the inventors on the development of a first-of-its-kind dissolvable tablet comprising peptide self-assemblies that are capable of acting as a sublingual vaccine.

One aspect of the present disclosure provides a method of formulating a tablet comprising peptide self-assemblies, the method comprising, consisting of, or consisting essentially of dissolving the peptide in water, fibrilizing with a buffer addition, adding a cryoprotectant, at least one excipient for tablet porosity and integrity, and an adjuvant, pipetting the fibrilized solution into a custom tray, and freezing and lyophilizing the solution to produce the tablet.

Another aspect of the present disclosure provides a vaccine formulated in tablet form produced by the methods provided herein. In one embodiment, the vaccine is additionally stable to heating for at least 1 week at 45° C. In some embodiments, the vaccine is specific for $M.$ $tuberculosis$. In certain embodiments, the vaccine comprises the epitope $ESAT_{51-70}$ for $M.$ $tuberculosis$.

In another aspect, the disclosure provides a dissolvable tablet formulation comprising (a) self-assembling peptide-polymer nanofibers comprising a peptide-polymer conjugate comprising (i) a self-assembling domain comprising a polypeptide and having a C-terminal and N-terminal end; (ii) a peptide epitope or protein antigen; and (iii) a mucus-inert domain, wherein (ii) and (iii) are linked to opposite ends of the (i) self-assembling domain; (b) an excipient; and (c) an adjuvant, wherein the dissolvable tablet is suitable for sublingual administration.

In a further aspect, the disclosure provides a method of eliciting an immune response against a peptide or protein antigen in a subject, the method comprising administering a therapeutically effective amount of the dissolvable tablet described herein sublingually to the subject.

In a further aspect, the disclosure provides a method of formulating a vaccine comprising dissolvable sublingual tablet, the method comprising the steps of: (i) combining a self-assembling peptide-polymer conjugate with a buffer to form a peptide-polymer nanofiber; (ii) adding at least one excipient and an adjuvant to the peptide-polymer nanofiber to form a vaccine solution; (iii) placing the vaccine solution into a mold; and (iv) removing the liquid from the vaccine solution to produce a tablet.

In further aspect, the disclosure provides a vaccine formulated in tablet form produced by the methods described herein.

Another aspect of the present disclosure provides all that is described and illustrated herein.

BRIEF DESCRIPTION OF THE DRAWINGS

FIG. 12 is a schematic summarizing the SIMPL tabletization process and use of the resulting SIMPL tablet vaccine.

DETAILED DESCRIPTION

Figure 1:
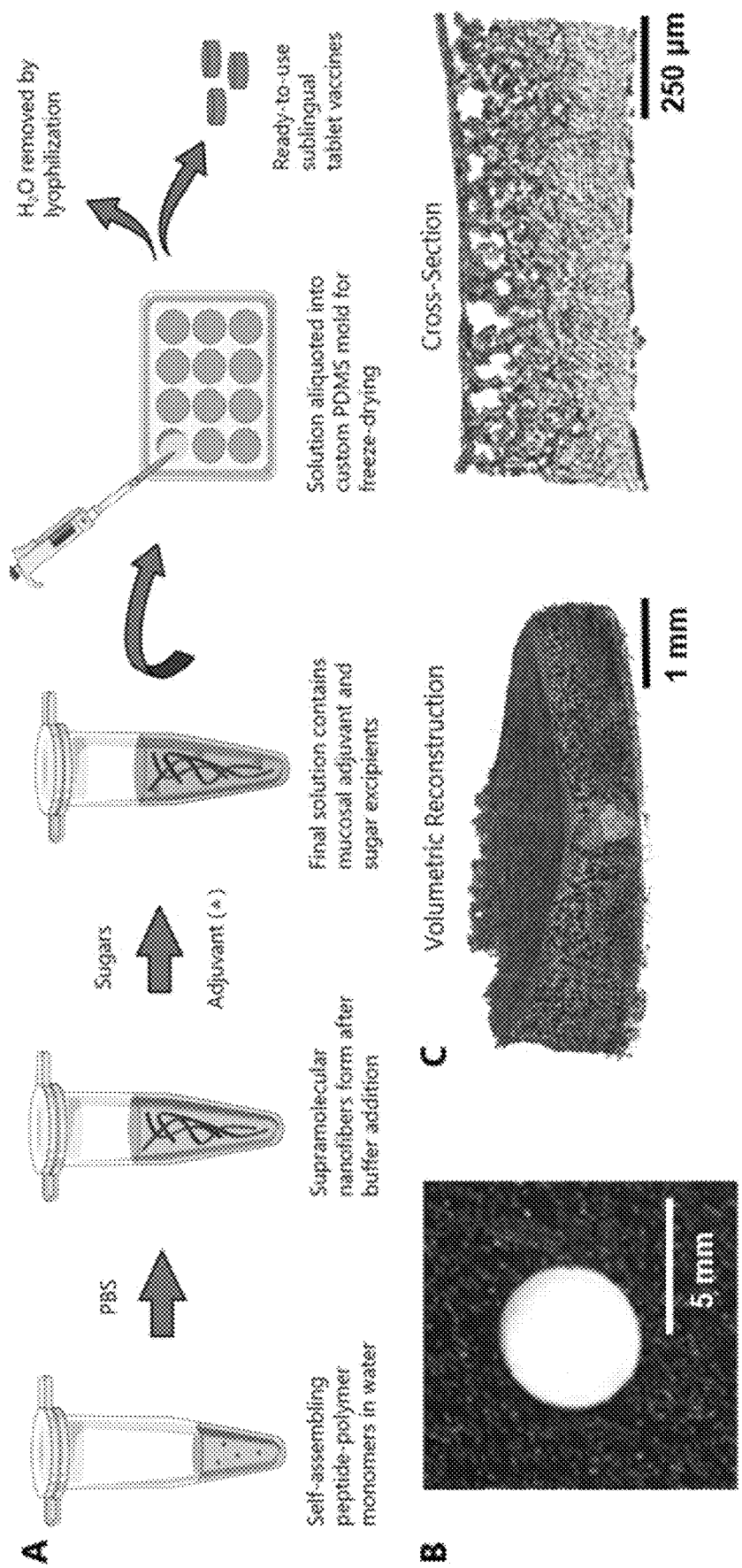
FIG. 1 demonstrates that the SIMPL tabletization process produces highly porous freeze-dried tablets that maintain nanofiber structure. (A) Schematic illustrating the production of SIMPL tablet vaccines. (B) Photograph of tablet. (C) Volumetric reconstruction and cross-section of tablet structure from microCT highlighting tablet porosity. (D) Contour plot showing combined effects of peptide and sugar concentration in tablets on elastic modulus. Tablets were prepared using nine combinations of peptide (OVAQ11) and sugar (dextran and mannose) concentrations (black dots on plot) and subjected to compressive testing using a microstrain analyzer. Trehalose concentration was held constant. n=3 tablets/group, mean values shown. Individual graphs showing effects of sugar and peptide concentration individually are in FIG. 5. (E-F) TEM images of Q11ESAT6 nanofibers prepared at 2 mM (E) or a tablet dissolved at 2 mM (F), each diluted to 0.2 mM before imaging. (G) β-sheet secondary structure was assessed by thioflavin T binding of a nanofiber solution before tabletization and of an equal concentration solution of a dissolved tablet. Excipient control contained no OVAQ11. ***$p<0.001$ by 1-way ANOVA with Tukey's multiple comparisons test, n=3/group.
Figure 1:
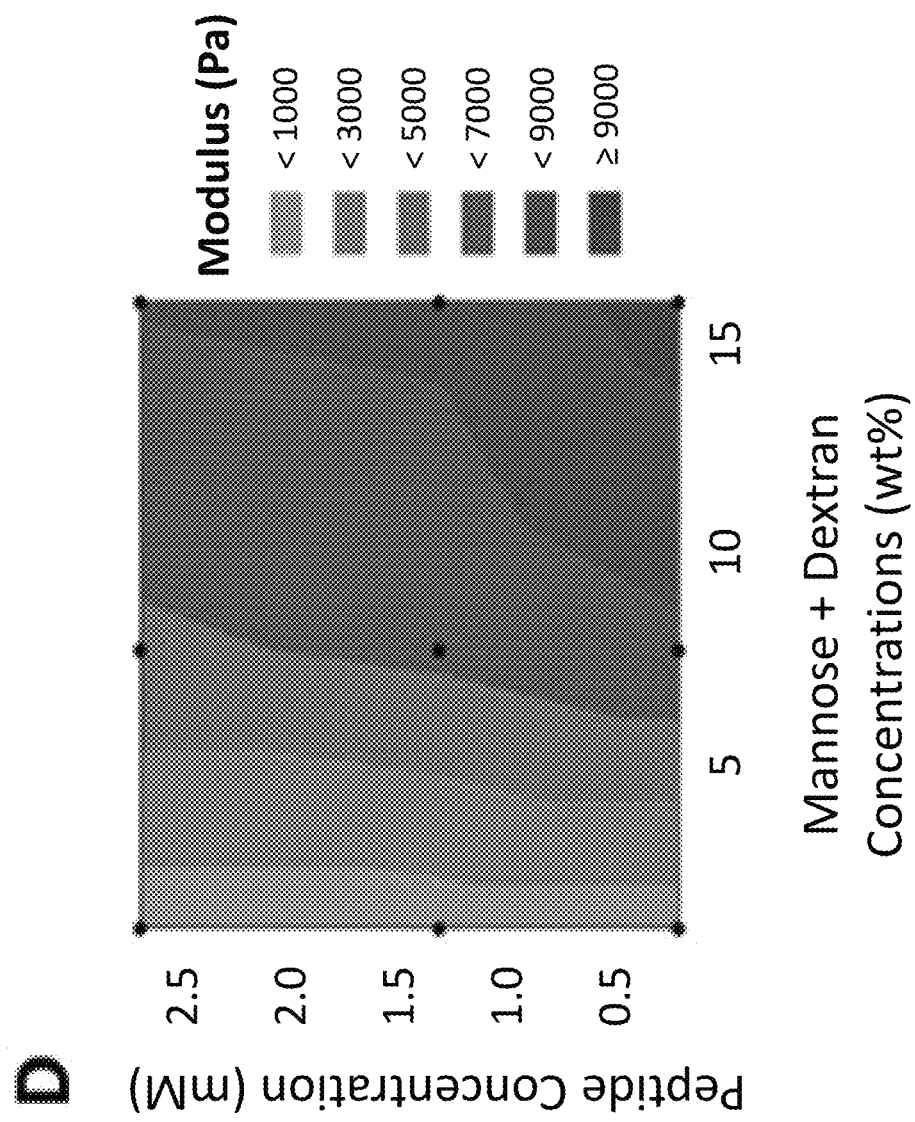
Figure 1:
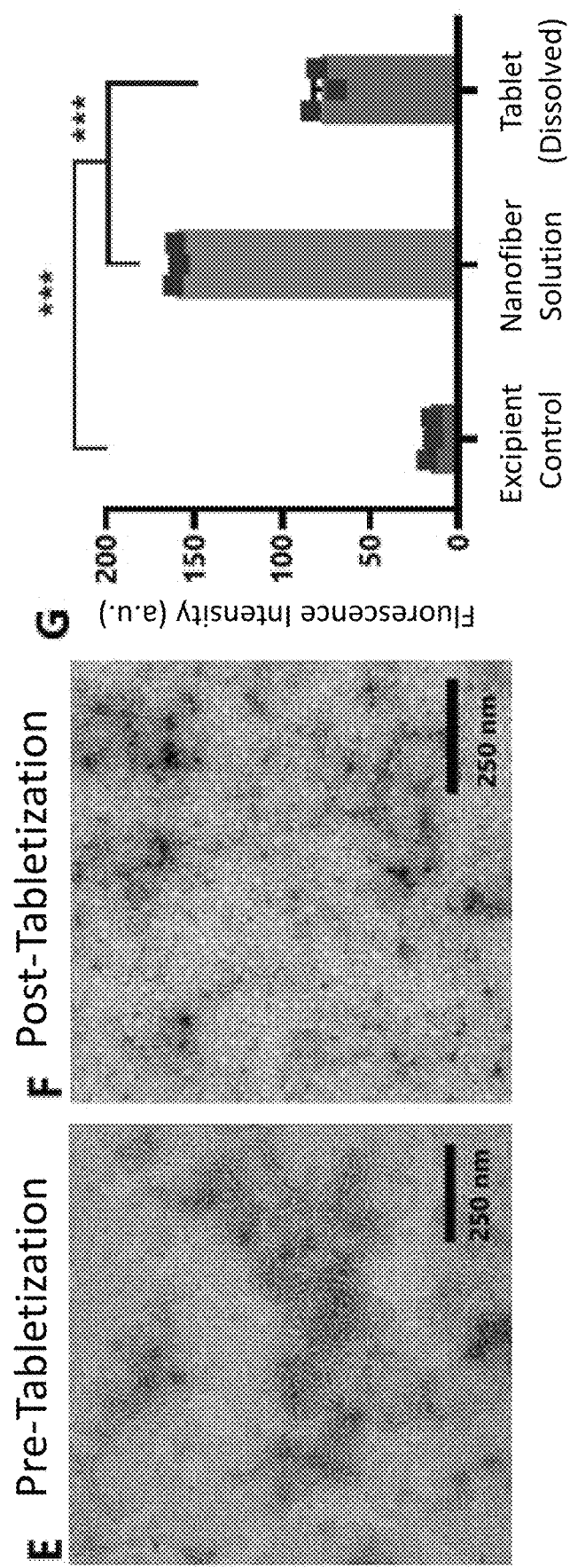

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

The present invention provides heat stable, dissolvable sublingual tablets for vaccination and eliciting immune responses. The present disclosure is based, in part, on the findings by the inventors on the development of a first-of-its-kind dissolvable tablet comprising peptide self-assemblies that are capable of acting as a sublingual vaccine.

The vast majority of clinically used vaccines are delivered via injection, which typically requires the involvement of trained personnel. In contrast, sublingual vaccine delivery (i.e., under the tongue) is needle-free, which provides both financial advantages and eliminates the chances of introducing new infections via contaminated needle reuse. Further, sublingual vaccine delivery has the potential for self-administration,[5-6] making it an ideal route for global vaccine distribution. Vaccines based on chemically defined biomaterials are increasingly being considered for infectious diseases[7] and have the potential for greater thermal stability than traditional vaccines based on attenuated pathogens. Despite this, sublingual biomaterial vaccines remain relatively unexplored due in part to challenges of delivery through the salivary mucus layer and long-term stability.

The present inventors recently reported the design of a liquid nanofiber vaccine based on self-assembling peptides (e.g., Q11) conjugated to mucus-inert materials such as polyethylene glycol (PEG) or random sequences of proline, alanine, and serine (PAS). These peptide-polymer assemblies can raise robust, antigen-specific responses against peptide epitopes that persist for at least a year when delivered sublingually. The inventors in the present invention have developed an improved tablet formulation made by the process to tabletize these nanofibers, producing a first-of-its-kind, heat-stable, and easily-administrable SIMPL (Supramolecular Immunization with Peptides SubLingually) tablet vaccine that dissolves under the tongue (see FIG. 12 for a schematic depiction) which provides additional benefits for storage, transport and accessibility for the vaccine compositions.

In one embodiment, the present invention provides a dissolvable tablet formulation comprising (a) self-assembling peptide-polymer nanofibers comprising a peptide-polymer conjugate comprising (i) a self-assembling domain comprising a polypeptide and having a C-terminal and N-terminal end; (ii) a peptide epitope or protein antigen; and (iii) a mucus-inert domain (e.g., polymer), wherein (ii) and (iii) are linked to opposite ends of the (i) self-assembling domain;(b) an excipient; and (c) an adjuvant, wherein the dissolvable tablet is suitable for sublingual administration.

Tablet Formulations

The present invention provides improvement over the prior vaccine composition by providing a heat stable tablet form for sublingual administration. The tablet has been given the name SIMPL (Supramolecular Immunization with Peptides SubLingually) tablet. The tablets are porous, strong, retain their shape and are readily disintegrable (i.e., dissolvable), allowing for packaging, storage and/or self-administration. The tablets have suitable porosity and microstructure that allows for adequate disintegration/dissolving during sublingual administration. Further, the tablet formulation allows for improved storage and shipping without reduction in the efficacy of the vaccine. The dissolvable tablet formulation comprising (a) self-assembling peptide-polymer nanofibers; (b) an excipient; and (c) an adjuvant are formulated in a dissolvable tablet for sublingual administration.

Suitable for sublingual administration means that the tablet is able to readily dissolve when placed in the oral cavity, preferably, under the tongue (sublingually) of an individual in need, and the active contents (e.g., self-assembling peptide-polymer) is able transport through the mucosal membrane in sufficient amounts to elicit an immune response.

The sublingual dosage described herein are tablets that are capable of disintegrating rapidly. The terms "disintegrating" or "dissolving" are used herein interchangeably to refer to the breakdown of the solid tablet and release of the active components when in contact with a liquid. The tablets of the present invention show a disintegration time from about 5 s to about 50 s, from about 5 s to about 40 s, or from about 5 s to about 30 s, e.g., dissolve in the oral cavity (e.g., under the tongue) in less than 50 seconds, alternatively less than 40 seconds, alternatively less than 30 seconds. In a further optional embodiment, the tablets of the present invention show a disintegration time from about 5 s to about 30 s. In this context, the term "disintegration time" can be measured by methods known in the art, for example, a measurement in pure water at 37° C. (e.g., USP disintegration tester (Erweka, ZT3)). Another method of measuring disintegration time include, for example, in human saliva, as described in Ali et al., Application of biorelevant saliva-based dissolution for optimisation of orally disintegrating formulations of felodipine, International Journal of Pharmaceutics, v. 555, 2019, p. 228-236, ISSN 0378-5173, (www.sciencedirect.com/science/article/pii/S0378517318308755), and Lagerlof F, Dawes C. The Volume of Saliva in the Mouth Before and After Swallowing. Journal of Dental Research. 1984; 63 (5):618-621. doi:10.1177/00220345840630050201, the contents of which are incorporated by reference in their entireties.

For example, in one embodiment, the tablets disintegrate in less than 1 minute, preferably less than 30 seconds, preferably in less than 10 seconds (e.g., about 5 s to about 60 s, preferably about 5 s to about 30 s) in 1.0 mL of human saliva at 37 C (1.0 mL is taken to be about the average volume of human saliva in the mouth).

Further, the tablet formulations described herein are heat stable. In some embodiments, the tablets are heat stable for at least 1 week at 45° C. The ability to be heat stable and retain activity at 45° C. for at least one week, which demonstrates that the tablets are able to be stored for long periods at room temperature and may be able to be exposed to fluctuating higher temperatures without breakdown of the active components or reduction in the efficacy of the active components to elicit an immune response.

The term "sublingual" refers to the route of administration by which a substance diffuses into the blood through the mucus membrane under the tongue. The mucus membrane refers to the membrane lining various cavities of the body, including the oral cavity, which functions as a barrier to exogenous pathogens and for hydrating body tissues. The mucus membrane under the tongue allows substances to diffuse into the blood through the membrane, which is predominantly a mucous gland that produces a thick mucinous fluid and lubricates the oral cavity (this mucus allows for swallowing, initiating digestion, buffering pH, and dental hygiene, etc.). The tablets described herein are made for predominantly sublingual administration. The tablets are molded into a suitable shape to allow for proper dissolution during sublingual administration, preferably dissolving in less than a minute, more preferably in less than 40 seconds when placed under the tongue.

The tablets described herein, when administered sublingually, are capable of eliciting an antibody response upon or after administration to a subject sublingually. Suitably, the tablets elicit a B cell response and antibodies against the peptide epitopes or antigen peptides contained with the self-assembling peptide-polymer nanofibers. FIG. 1D shows suitable concentrations of peptide-polymer complexes to excipients for use in the present application, which is described in more detail below.

The tablets described herein have the porosity suitable to provide the characteristics necessary for the tablet to be for sublingual administration, e.g., proper disintegration and strength for handling prior to administration. Porosity refers to the volume of the pores relative to the volume of the packed particles. Tablet porosity determines the tensile strength (hardness) of tablets for a given composition and the disintegration and dissolution kinetics, which depends on the tableting process. The mechanism of dissolution from porous tablets can be attributed to quick entry of water into porous matrix, which causes rapid disintegration and dissolution of the tablet.

The present technology has a porosity that provides hardness and strength that allows for the handling and manipulation of the tablet without breaking or crumbling, and the dissolution that allows for sublingual disintegration in less than a ninety (90) seconds, preferably in less than 1 minute (60 seconds), as detailed by the FDA for regulations for disintegration tablets, which can be found in "Guidance for Industry Orally Disintegrating Tablets" U.S. Department of Health and Human Services Food and Drug Administration Center for Drug Evaluation and Research (CDER), December 2008, the content of which is incorporated by reference in its entirety Self-Assembling Peptide Polymer Nanofibers The self-assembling peptide-polymer nanofibers used in the present invention are described in PCT Application No. PCT/US2018/042762, incorporated by reference in its entirety. The term "self-assembling peptide-polymer" refers to the ability of the polypeptide-polymer complexes described herein to form nanofibers, a supramolecular (self-assembling) complex, when placed into an isotonic solution.

The self-assembling domain comprising a polypeptide and having a C-terminal and N-terminal end. As used herein, the "self-assembling polypeptide" or "self-assembling domain" refers to a polypeptide that is able to spontaneously associate and form stable structures in solution, preferably a stable β-sheet. The self-assembling domain may also be referred to as a self-assembling peptide and the terms can be used interchangeably. In some embodiments, the self-assembling domain has a neutral net charge. In some embodiments, the self-assembling domain comprises a polypeptide having alternating hydrophobic and hydrophilic amino acids. Hydrophobic amino acids include, for example, Ala, Val, lie, Leu, Met, Phe, Tyr, Trp, Cyc, and Pro. Hydrophillic amino acids include, for example, Arg, His, Lys, Asp. Glu, Ser, Thr, Asn, and Gln.

In one example, the self-assembling polypeptide comprises a peptide in Table 1, for example, Q11 (SEQ ID NO:1). In another example, the self-assembling polypeptide comprises a peptide of SEQ ID NOs:1-67. Other self-assembling peptides can be used as described in more detail below. The self-assembling peptides may form β-sheets, α-helices, or other amphiphiles capable of forming nanofibers. In some embodiments, the present disclosure provides a polypeptide molecule comprising a self-assembling polypeptide at least 10 amino acids in length linked to the peptide epitope or antigen and the mucus-inert polymer as described herein. These polypeptide molecules can be assembled via isotonic solution into nanofibers, or supramolecular complexes.

Suitably, the self-assembling peptide is about 4 to about 40 amino acids in length, preferably about 10 to about 20 amino acids in length, and may include, for example, at least, at most, or exactly 4, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids. In some embodiments, the self-assembling polypeptide has at least some alternating hydrophobic and hydrophilic amino acids. In some embodiments, the self-assembling polypeptides are capable of forming a β-sheet. Hydrophobic amino acids include, for example, Ala, Val, lie, Leu, Met, Phe, Tyr, Trp, Cys, and Pro. Hydrophillic amino acids include, for example, Arg, His, Lys, Asp, Glu, Ser, Thr, Asn, and Gln. In some embodiments, the self-assembling domain is glutamine-rich. A glutamine-rich self-assembling domain may comprise a polypeptide wherein at least about 50%, at least about 55%, at least about 60%, at least about 65%, at least about 70%, at least about 75%, at least about 80%, at least about 85%, or at least about 90% of the amino acids are glutamine. In some embodiments, the self-assembling polypeptides form an α-helix. Amino acids that prefer to adopt helical conformations in a polypeptide include methionine (M), alanine (A), leucine (L), glutamate (E) and lysine (K).

Suitable examples of self-assembling polypeptides include, for example, those shown in Table 1. In some embodiments, the self-assembling domain includes a modification to the C-terminus, to the N-terminus, or to both the C-terminus and N-terminus. N-terminal modifications may include, for example biotin and acetyl. C-terminal modifications may include, for example, amino and amide. In some embodiments, modifications to the C-terminus and/or to the N-terminus include those shown in Table 1. In some embodiments, the self-assembling domain comprises a polypeptide selected from those listed in Table 1 but excluding an N-terminal and/or C-terminal modification shown in the table. Self-assembling polypeptides are also detailed in PCT/US2007/020754, PCT/US2017/025596, and are reviewed in Seroski and Hudalia, Self-Assembled Peptide and Protein Nanofibers for Biomedical Applications, Chapter 19 In Biomedical Applications of Functionalized Nanomaterials, (2018) 569-598, all of which are incorporated herein by reference. In addition, the self-assembling domain may be labeled with a detectable label such as a fluorescent molecule, detectable tag or enzyme capable of producing a detectable signal at either the N- or C-terminus. Such detectable labels are known to those of skill in the art and can be attached using routine methods including via a biotin-avidin linkage or amide bond formation.

TABLE 1 self-assembling polypeptides

| Name | Sequence | SEQ ID NO: |
|---|---|---|
| Q11 | QQKFQFQFEQQ | 1 |
| W-Q11 | WQQKFQFQFEQQ | 2 |
| EAK16-I | Ac-(AEAKAEAK)$_2$-NH$_2$ | 3 |
| EAK16-II | Ac-(AEAEAKAK)$_2$-NH$_2$ | 4 |
| EAK16-IV | Ac-AEAEAEAEAKKEAKKE-NH$_2$ | 5 |
| EMK16-11 | Ac-(MEMEMKMK)-NH$_2$ | 6 |
| RAD 16-1 | Ac-(RADARADA)$_2$-NH$_2$ | 7 |
| RAD 16-11 | Ac-(RARARDRD)$_2$-NH$_2$ | 8 |
| RAD 16-IV | Ac-RARARARARDRDRDRD-NH$_2$ | 9 |
| DAR16-IV | AC-ADADADADARARARAR-NH$_2$ | 10 |
| KLD16 | Ac-(KLDL)-NH$_2$ | 11 |
| FKFE2 | Ac-(FKFE)$_2$-NH$_2$ | 12 |
| EFK12 | Ac-(FKFE)-NH$_2$ | 13 |
| EFK16 | Ac-(FEFEFKFK)-NH2 | 14 |
| MAX1 | H$_2$N-VKVKVKVK-V$^D$PPT-KVKVKVKV-NH$_2$ | 15 |
| MAX2 (V16T) | H$_2$N-VKVKVKVK-V$^D$PPT-KVKTKVKV-NH$_2$ | 16 |
| MAX3 (V7T) | H$_2$N-VKVKVKTK-V$^D$PPT-KVKTKVKV-NH$_2$ | 17 |
| MAX4 | H$_2$N-KVKVKVKV-K$^D$PPS-VKVKVKVK-NH$_2$ | 18 |
| MAX5 (T12S) | H$_2$N-VKVKVKVK-V$^D$PPS-KVKVKVKV-NH$_2$ | 19 |
| MAX6 (V16E) | H$_2$N-VKVKVKVK-V$^D$PPT-KVKEKVKV-NH$_2$ | 20 |
| MAX7 (V16C) | H$_2$N-VKVKVKVK-V$^D$PPT-KVKCKVKV-NH$_2$ | 21 |
| MAX8 (K15E) | H$_2$N-VKVKVKVK-V$^D$PPT-KVEVKVKV-NH$_2$ | 22 |
| MAX9 (K2E) | H$_2$N-VEVKVKVK-V$^D$PPT-KVKVKVKV-NH$_2$ | 23 |
| MAX 10 (K4E) | H$_2$N-VKVEVKVK-V$^D$PPT-KVKVKVKV-NH$_2$ | 24 |
| MAX11 (K6E) | H$_2$N-VKVKVEVK-V$^D$PPT-KVKVKVKV-NH$_2$ | 25 |
| MAX12 (K8E) | H$_2$N-VKVKVKVE-V$^D$PPT-KVKVKVKV-NH$_2$ | 26 |
| MAX13 (K13E) | H$_2$N-VKVKVKVK-V$^D$PPT-EVKVKVKV-NH$_2$ | 27 |
| MAX14 (K17E) | H$_2$N-VKVKVKVK-V$^D$PPT-KVKVEVKV-NH$_2$ | 28 |
| P11-1 | Ac-QQRQQQOQEQQ-NH$_2$ | 29 |
| P11-2 | Ac-QQRFQWQFEQQ-NH$_2$ | 30 |
| P11-3 | Ac-QQRFQWQFQQQ-NH$_2$ | 31 |
| P11-4 | Ac-QQRFEWEFEQQ-NH$_2$ | 32 |
| P11-5 | Ac-QQOFOWOFQQQ-NH$_2$ | 33 |
| P11-7 | Ac-SSRFSWSFESS-NH$_2$ | 34 |
| P11-8 | AC-QQRFOWOFEQQ-NH$_2$ | 35 |
| P11-9 | Ac-SSRFEWEFESS-NH$_2$ | 36 |
| P11-12 | Ac-SSRFOWOFESS-NH$_2$ | 37 |
| P11-16 | Ac-NNRFOWOFEQQ-NH$_2$ | 38 |
| P11-18 | Ac-TTRFOWOFETT-NH$_2$ | 39 |
| P11-19 | AC-QQRQOQOQEQQ-NH$_2$ | 40 |
| 1 | Ac-FEFEFKFKFEFEFKFK-NH$_2$ | 41 |
| 2 | Ac-FEFEAKFKFEFEFKFK-NH$_2$ | 42 |
| 3 | Ac-FEFEFKLIEFEFKFK-NH$_2$ | 43 |
| 4 | Ac-FEAEVKLKIELEVKFK-NH$_2$ | 44 |
| 5 | AC-GEAEVKLKIELEVKAK-NH$_2$ | 45 |
| 6 | Ac-GEAEVKIKIEVEAKGK-NH$_2$ | 46 |
| 7 | Ac-IEVEAKGKGEAEVKIK-NH$_2$ | 47 |
| 8 | Ac-IELEVKAKGEAE KLK-NH$_2$ | 48 |
| 9 | Ac-IELEVKAKAEAEVKLK-NH$_2$ | 49 |
| 10 | Ac-IEAEGKGKIEGEAKIK-NH$_2$ | 50 |
| 11 | Ac-KKQLQLQLQLQLKK-NH$_2$ | 51 |
| 12 | Ac-EQLQLQLQLQLQE-NH$_2$ | 52 |
| 13 | Ac-KKSISLSLSLSLSLKK-NH$_2$ | 53 |
| 14 | Ac-ESLSLSLSLSLSLE-NH$_2$ | 54 |
| 15 | Ac-ECLSLCLSLCLSLE-NH$_2$ | 55 |
| 16 | IIIXGK-NH$_2$, wherein X is Q, S, N, G, L, or norvaline | 56 |
| KFE8 | Ac-FKFEFKFE-NH$_2$ | 57 |
| SLAC | KSLSLSLRGSLSLSLKGRGDS | 58 |
| Missing-tooth | KKSLSLSASLSLKK and KKSLSLSASASLSLKK together | 59 and 80 |
| CATCH (+) | Ac-QQKFKFKFKQQ-Am | 60 |
| CATCH (−) | Ac-EQEFEFEFEQE-Am | 61 |
| bQ13 | Ac-QQKFQFQFEQQQ-Am | 62 |
| Coil29 | QARILEADAEILRAYARILEAHAEILRAQ | 63 |
| PA1 | C$_{16}$H$_{31}$O-AAAAGGGEIKVAV-COOH | 64 |
| PA | C$_{16}$H$_{31}$O-CCCCGGGXGGGRGD-COOH, wherein X is phosphoserine | 65 |
| 17 | QAKILEADAEILKAYAKILEAHAEILKAQ | 66 |
| 18 | ADAEILRAYARILEAHAEILRAQ | 67 |

O is ornithine.

In some embodiments, the self-assembling domain comprises a polypeptide having an amino acid sequence of one of SEQ NOs:1-67 or a polypeptide with at least 75%, at least 80%, at least 85%, at least 90%, or at least 95% identity thereto. In some embodiments, the self-assembling domain comprises a polypeptide having an amino acid sequence of SEQ ID NO:1 (QQKFQFQFQFEQQ), or a polypeptide with at least 75%, at least 80%, at least 85%, at least 90%, or at least 95% identity thereto.

The self-assembling peptide is further linked to a peptide epitope or protein antigen and a mucus-inert polymer as described herein. The peptide epitope or protein antigen may be linked to either the N-terminal or C-terminal end, and is linked to the opposite end from the mucus-inert polymer. In some embodiments the peptide epitope or protein antigen is immunogenic, e.g., is able to elicit an immune response against the peptide or protein. The term "antigen" refers to a molecule capable of eliciting an immune response by being bound by an antibody (e.g. activation of 13 cell) or a T cell receptor (e.g., activation of T cells). The term "antigen", as used herein, includes B cell epitopes and also encompasses T-cell epitopes. An antigen is additionally capable of being recognized by the immune system and/or being capable of inducing a Immoral immune response and/or cellular immune response leading to the activation of B-lymphocytes and/or T-lymphocytes. In some embodiments, the antigen contains or is linked to a Th cell epitope. An antigen can have one or more epitopes (B-epitopes and T-epitopes). Antigens may include peptides, polypeptides, polynucleotides, carbohydrates, lipids, small molecules, and combinations thereof. Antigens may also be mixtures of several individual antigens. "Antigenicity" refers to the ability of an antigen to specifically bind to a T cell receptor or antibody and includes the reactivity of an antigen toward pre-existing antibodies in a subject. "Immunogenicity" refers to the ability of any antigen to induce an immune response and includes the intrinsic ability of an antigen to generate antibodies in a subject.

The term "peptide epitope" refers to a polypeptide of 3 to 50 amino acids. The peptide epitope may be linked to the N-terminal end or the C-terminal end of the self-assembling domain. In some embodiments, the peptide epitope is linked to the N-terminal end of the self-assembling domain. In some embodiments, the peptide epitope is linked to the C-terminal end of the self-assembling domain. In some embodiments, the peptide epitope is immunogenic. In some embodiments, the peptide epitope is antigenic.

In some embodiments, the peptide-polymer conjugate comprises a protein antigen. The "protein antigen" may comprise a polypeptide of 10 to 500 amino acids. In some embodiments, the peptide epitope is comprised within a protein antigen. In some embodiments, the peptide epitope is a portion of a protein antigen. The protein antigen may be linked to the N-terminal end or the C-terminal end of the self-assembling domain. In some embodiments the protein antigen is linked to the N-terminal end of the self-assembling domain. In some embodiments, the protein antigen is linked to the C-terminal end of the self-assembling domain. In some embodiments, the protein antigen is immunogenic. In some embodiments, the protein antigen is antigenic.

The peptide epitope or protein antigen can be any type of biologic molecule or a portion thereof in which one wishes to mount an immune response. Common categories of antigens include, but are not limited to, viral antigens, bacterial antigens, fungal antigens, protozoa and other parasitic antigens, tumor antigens, antigens involved in autoimmune disease, allergy and graft rejection, and other miscellaneous antigens. Antigens can be microbial antigens, such as viral, fungal, or bacterial; or therapeutic antigens such as antigens associated with cancerous cells or growths, or autoimmune disorders. In some embodiments, the peptide epitope comprises a B cell epitope or T cell epitope. In some embodiments, the peptide epitope comprises a B cell epitope and a T cell epitope. In some embodiments, the peptide epitope or protein antigen comprises an autologous target or a portion thereof. In some embodiments, the peptide epitope or protein antigen comprises a cytokine or a portion thereof.

In one embodiment, the peptide epitope or protein antigen is a viral antigen or portion or fragment thereof. Examples of viral antigens include, but are not limited to, for example, retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpl, gpll, and other varicella zoster viral antigen components; Japanese encephalitis viral antigens such as proteins E, M-E, M-E-NS 1, NS 1, NS 1 -NS2A., 80% E, and other Japanese encephalitis viral antigen components; rabies viral antigens such as rabies glycoprotein, rabies nucleoprotein and other rabies viral antigen components; or a portion thereof, SARS-CoV-2 viral proteins (e.g., spike, membrane, nucleocapsid, etc). See Fundamental Virology, Second Edition, e's. Fields, B. N. and Knipe, D. M. (Raven Press, New York, 1991) for additional examples of viral antigens.

In another embodiment, the peptide epitope or protein antigen bacterial antigen, portion or fragment thereof. Bacterial antigens may include, but are not limited to, for example, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diphtheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP6S), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; hemophilus influenza bacterial antigens such as capsular polysaccharides and other hemophilus influenza bacterial antigen components;

anthrax bacterial antigens such as anthrax protective antigen and other anthrax bacterial antigen components; rickettsiae bacterial antigens such as romps and other rickettsiae bacterial antigen component, or a portion thereof. Also included with the bacterial antigens described herein are any other bacterial, mycobacterial, mycoplasmal, rickettsial, or chlamydial antigens; or a portion thereof.

In another embodiment, the peptide epitope or protein antigen is a fungal antigen, or portion or fragment thereof. Fungal antigens may include, but are not limited to, *Candida* fungal antigen components; histoplasma fungal antigens such as heat shock protein 60 (FISP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components; or a portion thereof.

In another embodiment, the peptide epitope or protein antigen is a parasite antigen, or portion or fragment thereof. Examples of protozoa and other parasitic antigens may include, but are not limited to, *Plasmodium falciparum* antigens such as merozoite surface antigens, sporozoite surface antigens, circumsporozoite antigens, gametocyte/gamete surface antigens, blood-stage antigen pf 1 55/RESA and other plasmodial antigen components; toxoplasma antigens such as SAG-1, p30 and other toxoplasma antigen components; schistosomae antigens such as glutathione-S-transferase, paramyosin, and other schistosomal antigen components; leishmania major and other leishmaniae antigens such as gp63, lipophosphoglycan and its associated protein and other leishmanial antigen components; and trypanosoma cruzi antigens such as the 75-77 kDa antigen, the 56 kDa antigen and other trypanosomal antigen components; or a portion thereof.

In a further embodiment, the peptide epitope or protein antigen is a tumor antigen, portion or fragment thereof. Suitable tumor antigens may include, but are not limited to, telomerase components; multidrug resistance proteins such as P-glycoprotein; MAGE-1, alpha fetoprotein, carcinoembryonic antigen, mutant p53, immunoglobulins of B-cell derived malignancies, fusion polypeptides expressed from genes that have been juxtaposed by chromosomal translocations, human chorionic gonadotrpin, calcitonin, tyrosinase, papillomavirus antigens, gangliosides or other carbohydrate-containing components of melanoma or other tumor cells; or a portion thereof. It is contemplated that antigens from any type of tumor cell can be used in the compositions and methods described herein.

In another embodiment, the peptide epitope or protein antigen is an antigen relating to autoimmunity. Antigens involved in autoimmune diseases, allergy, and graft rejection can be used in the compositions and methods. For example, an antigen involved in any one or more of the following autoimmune diseases or disorders can be used: diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis. dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves opthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy may include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection may include antigenic components of the graft to be transplanted into the graft recipient such as heart, lung, liver, pancreas, kidney, and neural graft components. An antigen can also be an altered peptide ligand useful in treating an autoimmune disease.

Examples of miscellaneous antigens that can be can be used in the compositions and methods include endogenous hormones such as luteinizing hormone, follicular stimulating hormone, testosterone, growth hormone, prolactin, and other hormones, drugs of addiction such as cocaine and heroin, and idiotypic fragments of antigen receptors such as Fab-containing portions of an anti-leptin receptor antibody; or a portion thereof.

The peptide epitope or protein antigen may be conjugated or coupled to a self-assembling domain by any means known in the art, including, for example, click chemistry, Spytag/Spycatcher, oxime ligation, condensation reactions, in some embodiments, the peptide epitope or protein antigen is covalently coupled to the self-assembling domain. In some embodiments, the peptide epitope or protein antigen is attached to the self-assembling domain through a thiol reactive group. The peptide epitope or protein antigen may be covalently coupled to a terminus of the self-assembling domain. In some embodiments, the peptide epitope or protein antigen is covalently coupled to the N-terminus of the self-assembling domain. In some embodiments, the peptide epitope or protein antigen is covalently coupled to the C-terminus of the self-assembling domain.

The peptide epitope or protein antigen may be synthesized along with the self-assembling peptide by being encoded within a single polynucleotide that translates the entire self-assembling peptide and peptide epitope or protein antigen as a single polypeptide. Further, the peptide epitope or protein antigen may be linked to the N-terminal end or the C-terminal end of the self-assembling domain via a peptide linker.

A linker may be between the peptide epitope or protein antigen and the self-assembling domain. In some embodiments, the peptide epitope or protein antigen is attached to the self-assembling domain through a thiol reactive group in the linker. The peptide linker comprises a polypeptide of 3 to 10 amino acids, or 3 to 25 amino acids. In some embodiments, the peptide linker comprises a polypeptide having an amino acid sequence selected from SGSG (SEQ ID NO:68), $G_n$, wherein n is an integer from 1 to 10, $SGSG_n$ wherein n is an integer from 1 to 10 (SEQ ID NO:68), GSGS (SEQ ID NO:69), SSSS (SEQ ID NO:70), GGGS (SEQ ID NO:71), GGC, GGS, (GGC)$_8$, (G$_4$S)$_3$, and GGAAY (SEQ ID NO:72). The peptide linker may be cleavable by a protease. In some embodiments, the peptide linker comprises a polypeptide having an amino acid sequence of SEQ ID NO:68 (SGSG). In some embodiments, the conjugate includes more than one peptide linker. The peptide-polymer conjugate may include less than 20, less than 15, less than 10, or less than 5 peptide linkers. The peptide-polymer conjugate may include between 1 and 20, between 5 and 15, or between 1 and 5 peptide linkers. Multiple peptide linkers may be positioned adjacent to one another.

The peptides described herein, such as the self-assembling domain, the peptide epitope, and/or the peptide linker, can be chemically synthesized using standard chemical synthesis techniques. In some embodiments, the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides described herein. Techniques for solid phase synthesis are well known to those of skill in the art and are described, for example, by Barany and Merrifield (1963) Solid-Phase Peptide Synthesis; pp. 3-284 in The Peptides: Analysis, Synthesis, Biology. Vol. 2: Special Methods in Peptide Synthesis, Part A.; Merrifield et al. (1963) J. Am. Chem. Soc, 85: 2149-2156, and Stewart et al. (1984) Solid Phase Peptide Synthesis, 2nd ed. Pierce Chem. Co., Rockford, Ill. In some embodiments, the self-assembling peptide is synthesized by a solid phase peptide synthesis.

The proteins described herein, such as the protein antigen, may be produced recombinantly according to techniques known to those of skill in the art.

Mucus-Inert Domain

The self-assembling domain is further linked to a mucus-inert domain, preferably a mucus-inert polymer, e.g., polyethylene glycol or an amino acid polymer (e.g., random peptide sequence comprising proline (P), alanine (A) and serine (PAS)), that allows mucus-transport. In one embodiment, the mucus-inert domain is polyethylene glycol (PEG) domain. In another embodiment, the mucus-inert domain is a random sequence of proline, alanine, and serine (PAS) linked to the N-terminal end or the C-terminal end of the self-assembling domain.

"Polymer" or "synthetic polymer" refers to a polymer that is produced from at least one monomer by a chemical process. A synthetic polymer is not produced directly by a living organism. Synthetic polymers include a homopolymer, heteropolymer, block polymer, co-polymer, ter-polymer, etc., and blends, combinations and mixtures thereof. Examples of synthetic polymers include, but are not limited to, functionalized polymers, such as a polymer comprising 5-vinyltetrazole monomer units and having a molecular weight distribution less than 2.0. A synthetic polymer may be or contain one or more of a star block copolymer, a linear polymer, a branched polymer, a hyperbranched polymer, a dendritic polymer, a comb polymer, a graft polymer, a brush polymer, a bottle-brush copolymer and a crosslinked structure, such as a block copolymer comprising a block of 5-vinyltetrazole monomer units. Synthetic polymers include, without limitation, polyesters, poly(meth)acrylamides, poly(meth)acrylates, polyethers, polystyrenes, polynorbomenes and monomers that have unsaturated bonds. For example, amphiphilic comb polymers are described in U.S. Patent Application Publication No. 2007/00871 14 and in U.S. Pat. No. 6,207,749 to Mayes et al., the disclosure of each of which is herein incorporated by reference in its entirety. The amphiphilic comb-type polymers may be present in the form of copolymers, containing a backbone formed of a hydrophobic, water-insoluble polymer and side chains formed of short, hydrophilic non-cell binding polymers. Examples of other synthetic polymers include, but are not limited to, polyalkylenes such as polyethylene and polypropylene and polyethyleneglycol (PEG); polychloroprene; polyvinyl ethers; such as polyvinyl acetate); polyvinyl halides such as polyvinyl chloride); polysiloxanes; polystyrenes; polyurethanes; polyacrylates; such as poly(methyl (meth)acrylate), poly (ethyl (meth) aery late), poly(n-butyl(meth)acrylate), poly (isobutyl (meth)acrylate), poly(tert-butyl (meth)acrylate), poly(hexyl(meth)acrylate), poly(isodecyl (meth)acrylate), poly(lauryl (meth)acrylate), poly(phenyl (meth)acrylate), poly(methyl acrylate), poly(isopropyl acrylate), poly (isobutyl acrylate), and poly(octadecyl acrylate); polyacrylamides such as poly(acrylamide), poly(methacrylamide), poly(ethyl acrylamide), poly(ethyl methacrylamide), poly (N-isopropyl acrylamide), poly(n, iso, and tert-butyl acrylamide); and copolymers and mixtures thereof. These synthetic polymers may include useful derivatives, including synthetic polymers having substitutions, additions of chemical groups, for example, alkyl groups, alkylene groups, hydroxylations, oxidations, and other modifications routinely made by those skilled in the art. The synthetic polymers may include zwitterionic polymers such as, for example, polyphosphorycholine.

In one embodiment, suitable polymers for use in the present invention include, but are not limited to, PEG, PEG derivatives (e.g., methoxy-PEG, etc.) polypeptoids such as polysarcosine (poly(N-methylglycine)), Poly(2-alkyl-2-oxazolines) (POZs), Poly(vinyl alcohol) (PVA), Poly-(N-(2-hydroxypropyl)methacrylamide) (PHPMA), Poly(2-hydroxyethyl methacrylate) (pHEMA), Poly(2-hydroxyethyl acrylate) (PHEA), Polyglycidols (PGs), and Zwitterionic polymers, among others.

In a preferred embodiment, the mucus-inert domain is a polyethylene glycol (PEG) domain. The PEG domain includes at least one ethylene unit. The PEG do main is linked to the other of the N-terminal end and the C-terminal end of the self-assembling domain (from the peptide epitope or protein antigen). In some embodiments, the PEG domain is linked to the N-terminal end of the self-assembling domain. In some embodiments, the PEG domain is linked to the C-terminal end of the self-assembling domain. The PEG domain may have an average molecular weight of 300-5000 Da. The PEG domain may have an average molecular weight of at least about 300 Da, at least about 400 Da, at least about 500 Da, at least about 600 Da, at least about 700 Da, at least about 800 Da, at least about 900 Da, at least about 1000 Da, at least about 2000 Da, at least about 3000 Da, at least about 4000 Da, or at least about 5000 Da. The PEG domain may have an average molecular weight of less than about 5000 Da, less than about 4000 Da, less than about 3000 Da, less than about 2000 Da, or less than about 1000 Da. In some embodiments, the PEG domain has an average molecular weight of 350 Da (which may have a hydrodynamic radius of about 0.43 nm). In some embodiments, the PEG domain has an average molecular weight of 1000 Da (which may have a hydrodynamic radius of about 0.80 nm). In some embodiments, the PEG domain has an average molecular weight of 2000 Da (which may have a hydrodynamic radius of about 1.20 nm). In some embodiments, the PEG domain has an average molecular weight of 3000 Da (which may have a hydrodynamic radius of about 1.51 nm). The molecular weight may be calculated as the number average molecular weight. The PEG domain may be of the formula -(0-CH2—CH2)$_n$—OH, —(0-CH$_2$—CH$_2$)$_n$-0-C-|_4 alkyl, —(CH2—CH$_2$-0)$_n$—CH2-CH$_2$—OH, or —(CH$_2$—CH2-0)$_n$—CH2—CH$_2$-0-C$_1$.4 alkyl, wherein n is an integer between 1 and 200. In some embodiments, the PEG domain is of the formula —(O—CH2—CH2)n—OH or —(0-CH2—CH2)$_n$-0-C-|_4 alkyl for N-terminal PEGylation. In some embodiments, the PEG domain is of the formula —(CH2—CH2-0)$_n$—CH2—CH2—OH or —(CH2—CH2-0)$_n$—CH2—CH2-0-C"|4 alkyl for C-terminal PEGylation. In some embodiments, C-1.4 alkyl is methyl (for example, methoxy-terminated PEG, also referred to as mPEG). In some embodiments, C-|.4 alkyl is ethyl.

The PEG domain may be linked to the self-assembling domain by a linker. In some embodiments, the linker comprises a peptide linker as detailed above. In other embodiments, the linker comprises —NH2—, —COO—, or any suitable linker known by those of skill in the art. Linkers and methods of PEGylation are described in, for example, Turecek et al. (Journal of Pharmaceutical Sciences 2016, 105, 460-475).

The term "polymer" also includes amino acid chains, e.g., polypeptides, including linear and branched chains. In on embodiment, the polymer is a PAS peptide. In another embodiment, the polymer is a ZIPP peptide.

A PAS peptide or PAS sequence, as used herein, means an amino acid sequence comprising alanine (A), serine (S), and proline (P) residues, mainly alanine and serine residues, the amino acid sequence forming random coil conformation under physiological conditions. The PAS peptides may be about 5-50 amino acids in length, for example, about 10-30, e.g., about 20 amino acids in length. Accordingly, the PAS sequence may comprise, consist essentially of, or consist of alanine, serine, and proline which can be used as a part of the heterologous moiety. Under physiological conditions, a PAS peptide forms a random coil conformation. Non-limiting examples of the PAS peptides include AAPASPAPAAP-SAPAPAAPS (SEQ ID NO:73), APSSPSP-SAPSSPSPASPSS (SEQ ID NO:74), APSSPSP-SAPSSPSPASPS (SEQ ID NO:75), SSPSAPSPSSPASPSPSSPA (SEQ ID NO:76), AASPAAP-SAPPAAASPAAPSAPPA (SEQ ID NO:77), ASAAAPAAASAAASAPSAAA (SEQ ID NO:78), ASPAAPAPASPAAPAPSAPA (SEQ ID NO:79) or any variants, derivatives, fragments, or combinations thereof and are not limited by the embodiments described herein. Additional examples of PAS sequences are known from, e.g., US Pat. Publ. No. 2010/0292130 A1, PCT Appl. Publ. No. WO 2008/155134 A1, and EP2173890, contents of which are incorporate by reference in their entirety.

In another embodiment, the polymer is a ZIPP peptide. A ZIPP peptide is a zwitterionic polypeptides (ZIPPs) with a repetitive (VPX$_1$X$_2$G)$_n$ motif (SEQ ID NO:89), where X$_1$ and X$_2$ are cationic and anionic amino acids, respectively, and n is the number of repeats. Suitable ZIPP peptides are described in, for example, Banskota, Samagya et al. "Long circulating genetically encoded intrinsically disordered zwitterionic polypeptides for drug delivery." *Biomaterials* vol. 192 (2019): 475-485. doi:10.1016/j.biomaterials.2018.11.012, the contents of which are incorporated by reference, and Banskota S, Saha S, Bhattacharya J, Kirmani N, Yousefpour P. Dzuricky M, Zakharov N, Li X, Spasojevic I, Young K. Chilkoti A. Genetically Encoded Stealth Nanoparticles of a Zwitterionic Polypeptide-Paclitaxel Conjugate Have a Wider Therapeutic Window than Abraxane in Multiple Tumor Models. Nano Lett. 2020 Apr. 8; 20 (4): 2396-2409. doi: 10.1021/acs.nanolett.9b05094. Epub 2020 Mar. 9. PMID: 32125864, the contents of which are incorporated by reference. For example, suitable ZIPP peptides include, but are not limited to, (VPKEG)$_n$ (X1=K, X2=E) (SEQ ID NO:90), (VPREG)$_n$ (SEQ ID NO:91), (VPKDG)$_n$ (SEQ ID NO:92), and (VPRDG)$_n$ (SEQ ID NO:93), wherein n is an integer from 20-160.

The mucus-inert domain is preferably attached the opposite end of the self-assembling polypeptide from the peptide epitope or antigen.

Excipient

The term "excipient" refers to inactive components or ingredients used in the formulation of the dissolvable tablets herein. The tablets of the present invention provide one or more excipients that allow for the formation of suitable microstructure and porosity within the tablet to allow for sublingual administration. Excipients include components such as diluents or fillers, binders, disintegrants, lubricants, coloring agents, flavoring or sweeteners, suspending agents, pH adjusting agents, preservatives, and combinations thereof. The excipients can alter the chemical and physical properties of the tablet affecting the biopharmaceutical profile. Suitable excipients for the present sublingual tablets are suitable components that allow for the strength and porosity needed to provide the correct microstructure for sublingual administration. In a preferred embodiment, the excipients are one or more sugar, including sugar alcohols. Sugar alcohol refers to polyhydroxy alcohols that include acyclic or alicyclic polyols. Acyclic sugar alcohols have the general formula CnHn+2(OH)n. Typical sugar alcohols include, for example, mannitol, sorbitol, xylitol, lactitol, isomalt, maltitol, erythritol, and threitol. Preferred sugar alcohols are those containing four to six carbon atoms (i.e, n is 4 to 6), especially five or six carbon atoms (n is 5 or 6). A particularly preferred sugar alcohol is mannitol [(C6H8(OH)6)] [(2R,3R,4R,5R)-hexane-1,2,3,4,5,6-hexol] [CAS #69-65-8]. Mannitol is non-hydroscopic, produces solutions with relatively low viscosity, and has a relatively high melting point (about 167-170° C.). Additional suitable sugars are known in the art and include, but are not limited to, for example, glucose, lactose, dextrose, dextran, and sucrose. Dextran is a polysaccharide consisting of glucose monomers linked mainly by α(1-6) bonds, produced by numerous microorganisms.

Other excipients ay be used in the practice of the present invention include lubricants, binders, disintegrants, colorants, and flavorants. Suitable lubricants include, for example, silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of theobroma. Suitable binders include, for example, polyvinyl pyrrolidone; magnesium aluminum silicate; starches such as corn starch and potato starch; gelatin; tragacanth; sucrose; and cellulose and its derivatives, such as sodium carboxymethylcellulose, ethyl cellulose, methylcellulose, microcrystalline cellulose, and hydroxypropyl methylcellulose. Suitable disintegrants include, for example, agar, alginic acid and the sodium salt thereof, effervescent mixtures, croscarmelose, crospovidone, sodium carboxymethyl starch, sodium starch glycolate, clays, and ion exchange resins. Suitable colorants include, for example, a colorant such as an FD&C dye. Suitable flavors include, for example, menthol, peppermint, and fruit flavors. Suitable sweeteners include, for example, aspartame and saccharin, or a combination thereof. Suitable antioxidants include, for example, butylated hydroxyanisole ("BHA"), butylated hydroxytoluene ("BHT"), and vitamin E. Suitable preservatives include, for example, benzalkonium chloride, methyl paraben, and sodium benzoate.

The excipients comprises at least 5% to 50% by weight of the solution before tabletization, for example, from about 15% to about 305% by weight.

In another embodiment, the total excipients comprise about 20% to about 30% w/v of the solution prior to tabletization, for example, about 22% to about 25% w/v (e.g., 22%, 23%, 24%, 25% w/v).

In a preferred embodiment, the one or more excipients is mannitol and dextran. Suitable ranges of the amount of mannitol and dextran would be calculated by one skilled in the art, for the proper microstructure having the proposer sizing, hardness and porosity for sublingual administration, as demonstrated in the examples.

In order to obtain a solid microstructure, the ratio of dextran to mannitol should be controlled. In a preferred embodiment, the ratio of dextran to mannitol is from about 2:20 to about 20:1, more preferably from about 2:10 to about 10:1. In yet a further embodiment the ratio of starch to mannitol is 1:1.

The solid dosage form according to the present invention is manufactured from a dosing solution, which is first frozen and then freeze-dried. In a preferred embodiment the content of dextran is between about 1-20% W/W of the dosing solution and the content of mannitol is between about 1-20% W/W of the dosing solution. In another preferred embodiment the content of starch is between about 2-10% W/W of the dosing solution and the content of mannitol is between about 2-10% W/W of the dosing solution. In yet a further preferred embodiment the content of starch is between about 3-10% W/W of the dosing solution and the mannitol is between about 3-10% W/W of the dosing solution. In another embodiment the matrix comprises about 5-10.% W/W starch of the dosing solution and about 5-10% W/W mannitol of the dosing solution In further embodiments, the tablet may further comprise a cryoprotectant. A cryoprotectant is an agent that reduces ice formation within a solution during the freezing process reducing damage to proteins included within the solution. Suitable cryoprotectants are known in the art and include, but are not limited to, for example, trehalose, glucose, fructose, sorbitol, mannitol, sucrose, raffinose, among others.

Adjuvant

The tablets of the present invention further comprise one or more adjuvants, preferably a mucosal adjuvant. An adjuvant is an agent that improves the immune response to a vaccine, e.g., an antigenic peptide or protein. Suitable adjuvants are known in the art, and particularly, the mucosal adjuvants are known in the art. For example, adjuvants may include, but are not limited to, cholera toxin, CpG, cyclic-di-GMP, cyclic-di-AMP, or a combination thereof. Cholera toxin may include, for example, Cholera Toxin B (CTB).

The present invention further provides a vaccine formulated in sublingual tablet form produced by the methods described herein. The tablet comprises the peptide-polymer nanofiber described herein. The vaccine is additionally stable to heating for at least 1 week at 45° C. Further, the vaccine is stable for storage at room temperature (about 25-30° C.) for at least one month or more, alternatively for at least two months or more, alternatively for at least three months or more. The vaccine can be specific for a bacteria, a virus or a fungus, or other antigens, as described herein.

The vaccine may be for bacteria, preferably M. tuberculosis. Suitable epitopes for M. tuberculosis are known in the art, including, for example, the epitope $ESAT_{51-70}$ from M. tuberculosis.

The present invention further comprises a dissolvable tablet form. The term "dissolvable tablet form" refers to dosage forms which disintegrate in less than about 90 seconds, preferably in less than about 60 seconds, preferably in less than about 30 seconds, more preferably in less than about 20, even more preferably in less than about 10 seconds when administered sublingually. The tablet may be a solid dosage form including, for example, tablets, capsules, lozenges or caplets.

The solid forms or tablets comprising the peptide-polymer nanofibers described herein are non-compressed. The term "non-compressed" refers to a solid dosage form, which is manufactured by removal of a liquid from a solution comprising the active ingredient and excipients resulting in a vaccine in tablet form. The term "solid form" refers to a unit dosage form that is not a liquid, or a powder when it is administered in the oral cavity, thus "solid dosage forms" refers to e.g. tablets containing a unit dose of the active ingredient.

The term tablets, solid dosage and vaccine form are used interchangeably herein.

Methods

The present disclosure further provides method of eliciting an immune response against a peptide epitope or protein antigen in a subject. The method comprises administering a therapeutically effective amount of the dissolvable tablet described herein sublingually to the subject. The tablet described herein may elicit an antibody or immune response to the peptide epitope or antigen. In some embodiments, the tablet elicits a humoral immune response. In some embodiments, the tablet elicits a cellular immune response. In some embodiments, the tablet elicits humoral and cellular immune responses. In some embodiments, the tablet elicits a T cell response.

The term "therapeutically effective amount" or "therapeutically effective" refers to the amount capable of eliciting a measurable immune response. A therapeutically effective amount of a peptide-polymer nanofiber comprised within the tablet, complex, or composition thereof, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The tablet is preferably delivered sublingually. Sublingual administration is through the mucosa of the floor of the mouth and ventral side of the tongue. Mucosal vaccines, which are vaccines delivered across the mucosal barriers through which most pathogens enter the body, may have key advantages over vaccines delivered through systemic injection via needles. Immunologically, these vaccines can elicit protective antibodies in mucosal compartments to neutralize and clear pathogens from the body before they take up residence. Furthermore, depending on the chosen mucosal delivery route, these vaccines may have significant logistical and financial benefits. The tablets provided herein for sublingual administration further provide heat stable forms, which allows for storage and transportation of the tablets thereof. Sublingual vaccination may also be a favorable delivery route to encourage compliance, as it does not require needles, thereby allowing for pain-free and potentially self-administered vaccination using dissolvable tablets or wafers. Because it does not require needles or trained personnel, sublingual immunization can be done at a lower cost, which may be constraints when designing vaccines for developing nations. Sublingual administration may also reduce or prevent the reuse of needles, and thereby prevent or reduce infections.

Upon sublingual administration, the peptide-polymer nanofiber may penetrate through the salivary mucus layer and be sampled by antigen presenting cells (e.g., dendritic cells) at the sublingual epithelium. Mucus is composed largely of mucins, which are glycoprotein fibers that crosslink and entangle to form a network that may restrict the movement of pathogens through mucus barriers to promote clearance from the body. Without being limited to theory, it may be that the PEG domain of the peptide-polymer conjugate detailed herein may reduce or prevent interactions with the mucus network, thereby minimizing mucosal-adhesion and promoting diffusion. The PEG domain may reduce binding of mucin to the peptide-polymer conjugates. Mucin binding to the peptide-polymer conjugates may be negatively correlated with the molecular weight of the PEG domain. Mucin binding affinity may not be correlated with the molecular weight of the PEG domain.

The present disclosure also provides methods of immunizing a subject. The method may include administering to the subject an effective amount of the tablet, composition or peptide-polymer nanofiber thereof as detailed herein. In some embodiments, the tablet is administered sublingually. Further provided is an antibody produced by an immunized subject as detailed herein.

In some embodiments, the immune response is an antigen-specific immune response. In some embodiment, the antigen-specific immunity is life-long. In some embodiments, the antigen-specific immunity is temporary and/or not lifelong. Antigen-specific immunity refers to an adaptive immune response that occurs upon subsequent encounter with an antigenic determinant. In life-long immunity, vaccination protects the subject from environmental encounters with the antigen by inducing an immune response after the antigen has been encountered. In some embodiments, the immunity is temporary or lasts less than 20, 15, 10, 9, 8, 7, 6, 5, 4, 3, 2, or 1 years (or any derivable range therein). In some embodiments, the immune response comprises IgG1 antibody isotypes. In some embodiments, IgG1 antibody isotypes are the dominant antibody isotype produced in the immune response. In some embodiments, IgG1 antibody isotypes are significantly more in relation to the other antibody isotypes in the immune response. In some embodiments, the titer of IgG1 is at least 1, 1.5, 2, 2.5, or 3 log 10 units higher than other isotypes.

In some embodiments, the tablet or composition thereof may confer protective immunity to a subject. Protective immunity refers to a subject's ability to mount a specific immune response that protects the subject from developing a particular disease or condition that involves the agent against which there is an immune response. An immunogenically effective amount is capable of conferring protective immunity to the subject. Different polypeptides as detailed herein may have different functionalities. While according to one aspect, a polypeptide is derived from an antigen or immunogen designed to induce an active immune response in a recipient. The phrase "immune response" or "immunological response" refers to the development of a humoral (antibody mediated), cellular (mediated by antigen-specific T cells or their secretion products), or both humoral and cellular response directed against an antigen, epitope, protein, peptide, carbohydrate, or polypeptide in a recipient patient. Such a response can be an active response induced by administration of an epitope or antigen or immunogen. A cellular immune response may be elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils or other components of innate immunity. As used herein "active immunity" refers to any immunity conferred upon a subject by administration of an epitope or antigen.

To induce an immune response, the tablet may be dissolved sublingually and the peptide-polymer nanofiber may be taken up by an antigen presenting cell (APC), processed, and presented on a major histocompatibilty complex (MHC). In some embodiments, the immune response can protect against or treat a subject having, suspected of having, or at risk of developing an infection or related disease, or a pathological condition such as cancer or autoimmunity. The tablets can be used to provide effective vaccines, such as microbial vaccine or cancer vaccines. The tablets detailed herein may induce an immune response. The immune response may be an antigen-specific immune response. Administration of the peptide-polymer nanofibers and tablets thereof may raise antibodies specific to the peptide epitope or protein antigen thereof. In some embodiments, the immune response includes or favors a Th2 response. In some embodiments, the antigen-specific immune response is temporary or not life-long. In some embodiments, the immune response comprises IgG1 antibody isotypes. In some embodiments, the immune response is an anti-cancer immune response. The peptide-polymer nanofibers and tablets thereof, may have increased immunogenicity relative to a control. For purposes of this specification and the accompanying claims, the terms "epitope" and "antigenic determinant" may be used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by 3H-thymidine incorporation by primed T cells in response to an epitope (Burke et al., 1994), by antigen-dependent killing (cytotoxic T lymphocyte assay, Tigges of al., 1996) or by cytokine secretion.

The presence of a cell-mediated immunological response can be determined by proliferation assays (CD4 (+) T cells) or CTL (cytotoxic T lymphocyte) assays. As used herein and in the claims, the terms "antibody" or "immunoglobulin" are used interchangeably and refer to any of several classes of structurally related proteins that function as part of the immune response of an animal or recipient, which proteins include IgG, IgD, IgE, IgM and related proteins. Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

Method of Making

The present invention also provides methods of formulating a vaccine comprising a dissolvable sublingual tablet. The methods comprise the steps of: (i) combining a self-assembling peptide-polymer conjugate with a buffer to form a peptide-polymer nanofiber; (ii) adding at least one excipient and an adjuvant to the peptide-polymer nanofiber to form a vaccine solution; (iii) placing the vaccine solution into a mold or custom tray; and (iv) removing the liquid from the vaccine solution to produce a tablet. In some embodiments, step (iv) comprises freezing and lyophilizing the solution to produce the tablet. Step (i) combining a self-assembling peptide-polymer conjugate with a buffer to form a peptide-polymer nanofiber comprises a suitable buffer that allows for self-assembly. For example, suitable buffers include phosphate buffer saline (PBS), buffered saline, and the like. Other suitable buffers include, but are not limited to Hanks Balanced Salt Solution (HBSS), MOPS, HEPES, DIPSO, carbonate, phosphate, among others. Once the peptide-polymer nanofiber is created, the nanofiber is mixed with at least one excipient and an adjuvant to form a vaccine solution. One or more cryoprotectants may also be added to the vaccine solution before tablet formation. The vaccine solution is then placed into a mold or tray. The mold or tray is of suitable size to provide the dosage of the peptide-polymer nanofiber contemplated herein. Suitable molds are known and can be developed in the art. For example, suitable molds or trays may be made of plastic, silicone, polydimethylsiloxane (PDMS), or the like.

Preferably, pH is adjusted prior to solidification of the solution to avoid denaturation of the peptide-polymer nanofiber and assure a stable product. Preferably, compositions containing the polymer-peptide nanofiber should be adjusted to pH between 3.5-10, more preferably 4-9, most preferably 6-9.

Methods of removing the liquid from the vaccine solution in the mold are known in the art. For example, the mold containing the solution may first be frozen and then lyophilized, i.e., freeze-dried. Lyophilization (which is also known as freeze-drying) is a technique for removing moisture from a wet material by freezing it and subsequently subliming moisture from it under reduced pressure. In this process, a suspension, solution or wet solid is frozen, and ice crystals in the frozen product are removed through a sublimation process at a reduced temperature and pressure that transforms ice directly into a vapor. The resulting freeze-dried product is a porous mass about the same size and shape as the original frozen mass. It has good stability, convenient reconstitutability when placed in solvent (usually water), and maintains flavor and texture similar to the original material.

Typical freeze-drying operations are known and understood in the art. Freeze-drying can require three steps: freezing, removal of unbound liquid (primary drying) by sublimation from a solid directly into a vapor, and desorption of bound solvent (secondary drying) from a liquid into a vapor. Materials to be freeze-dried may be complex mixtures of solvent(s) and other substances that are cooled to form ice crystals. With further cooling, the mass becomes more rigid as the result of formation of eutectics. When the entire mass is solidified, all unbound solvent has been transformed into ice. Bound solvent, however, remains fixed as a liquid within the internal structure of the material and is not frozen.

During the sublimation phase of freeze-drying, the frozen material is exposed to a vacuum, and heat is applied to the ice crystals to sublime them. The temperature and pressure of the lyophilization process is carefully controlled such that the frozen mass is maintained below the eutectic temperature at which the mass begins to melt. Maintaining the temperature of the treated mass lower than its eutectic temperature is considered critical to providing a freeze-dried product. See, for example, U.S. Pat. Nos. 4,616,047 and 4,001,944, which stress that lyophilization occurs below the initial melting temperature of the mass. Removing unbound solvent during the primary drying step is therefore accomplished without exceeding the eutectic temperature of the composition. Direct sublimation from a solid to a vapor has been considered important to forming the microporous structure that gives freeze-dried products their porosity and reconstitutability.

Lyophilization processes have been used to prepare tablets that are described as rapidly dissolving in a subject's mouth. Such, tablets are shown in U.S. Pat. Nos. 4,371,516 and 4,946,684, as well as GB 2,111,423 as exemplary and not limited to these disclosures. These patents disclose pharmaceutical tablets having an open matrix network structure containing gelatin or a natural gum and a carbohydrate such as mannitol. U.S. Pat. No. 4,946,684, for example, describes tablets containing mannitol and gum that are prepared by a lyophilization process in which the tablet is initially frozen. Moisture is then sublimed from the tablet below the initial melting temperature of the mixture. Direct sublimation of liquid from the tablet has been found to produce a very porous open matrix network throughout the tablet into which saliva rapidly moves to disintegrate the lyophilized mass after it is placed in a subject's mouth. In another embodiment, the method of lyohpylization described in Wilkhu, Minder S et al. "Development of a solid dosage platform for the oral delivery of bilayer vesicles." European journal of pharmaceutical sciences: official journal of the European Federation for Pharmaceutical Sciences vol. 108 (2017): 71-77. doi:10.1016/j.ejps.2017.06.014, can be used, and is incorporated by reference in its entirety. For example, lyophilisation can be performed such as a primary drying to occur at −40° C. for 48 h with a secondary drying cycle set at 20° C. for a further 10 h with a condenser temperature set at −75° C.

The method described herein provide a tablet with a suitable microstructure for sublingual administration.

The present disclosed vaccines could be used to prevent or treat a disease or condition. As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

Unless otherwise defined, all technical terms used herein have the same meaning as commonly understood by one of ordinary skill in the art to which this disclosure belongs. One aspect of the present disclosure provides a method of formulating a tablet comprising peptide self-assemblies, the method comprising, consisting of, or consisting essentially of dissolving the peptide in water, fibrilizing with a buffer addition, adding a cryoprotectant, at least one excipient for tablet porosity and integrity, and an adjuvant, pipetting the fibrilized solution into a custom tray, and freezing and lyophilizing the solution to produce the tablet.

Another aspect of the present disclosure provides a vaccine formulated in tablet form produced by the methods provided herein. In one embodiment, the vaccine is additionally stable to heating for at least 1 week at 45° C. In some embodiments, the vaccine is specific for *M. tuberculosis*. In certain embodiment, the vaccine comprises the epitope ESAT51-70 for *M. tuberculosis*.

Articles "a" and "an" are used herein to refer to one or to more than one (i.e., at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result, and preferably refers to +/−10% of the value.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising." Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

All publications, patent applications, patents, and other references mentioned herein are incorporated by reference in their entirety. In the case of conflict, the present specification, including definitions, will control.

Other features and advantages of the invention will be apparent from the description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting.

EXAMPLES

Widespread vaccination is essential to global health. Significant barriers exist to improving vaccine coverage in lower- and middle-income countries, including the costly requirements for cold-chain distribution and trained medical personnel to administer the vaccines. In the following Example, the inventors disclose a heat-stable and highly porous tablet vaccine that they designed to be administered sublingually via simple dissolution under the tongue. The inventors produced these SIMPL (Supramolecular Immunization with Peptides SubLingually) tablet vaccines by freeze-drying a mixture of self-assembling peptide-polymer nanofibers, sugars, and adjuvant. They demonstrate that sublingual immunization with SIMPL tablets raised antibody responses against both a model epitope from ovalbumin and a clinically relevant epitope from *M. tuberculosis*. Further, they show that sublingual antibody responses were not diminished after heating the tablets for 1 week at 45° C., in contrast to a more conventional carrier vaccine (KLH). Their novel vaccine approach directly addresses the need for a heat-stable and easily deliverable vaccine to improve equity in global vaccine coverage.

Materials and Methods

Peptide Synthesis: Peptides were synthesized using Fmoc solid phase synthesis, cleaved with trifluoroacetic acid, and precipitated in diethyl ether prior to purification by RP-HPLC on a C4 column. Conjugation of $PEG_{3000}$ to the C-terminus of OVAQ11 and pOVA and mPEth2000 conjugation to the N-terminus of Q11ESAT6, Q11PepIroN, Q11PepIutA, and Q11PepIreA were performed as described.[8] See Table 2 for the sequences of the peptides used in this study. Biotinylation and conjugation of fluorescent TAMRA were performed as described.[21] Peptide identity was confirmed using MALDI mass spectrometry. KLH-ESAT6 conjugates were prepared as described[22] using Cys-ESAT6 peptide and Imject Maleimide Activated mcKLH Kit (Thermo Scientific, cat #77666).

SIMPL Tabletization Process: Reverse tablet molds were designed in FreeCAD and 3D-printed with a MakerBot Ultimaker 3. PDMS molds were prepared using SYLGARD 184 kits (Sigma, cat #761028). Peptide solutions were prepared at 2 mM in 1×PBS, incubated for 3-4 h at room temperature to fibrillize, and mixed with sugars to a final concentration of 0.3 mM peptide and 7.8 wt % each of trehalose (Santa Cruz Biotechnology, cat # 394303), dextran (Alfa Aesar, cat #J61216), and mannitol (Sigma, cat #M4125). Adjuvanted formulations contained cholera toxin B (List Biological, cat #104) or Vaccigrade cyclic-di-AMP (Invivogen, cat #vacnacda) at doses indicated in figure captions. Final solutions were pipetted into the PDMS tray (30 μL per tablet), frozen at −80° C., and lyophilized. Heating was performed by placing individual tablets in microcentrifuge tubes in a heating block set at 45° C. KLH groups were heated as solutions in their final formulation.

Uropathogenic E. coli. (UPEC) Tablet Synthesis: To prepare tablets containing co-assembled peptides, PEG-Q11PepIreA, PEG-Q11PepIutA, and PEG-Q11PepIroN were weighed out and the dry powders were vortexed for 30 minutes. The peptide mixture was dissolved in a solution of VACQ11, briefly sonicated, and incubated overnight at 4° C. Control tablets without VACQ11 were dissolved in a solution of Q11. Preparation then continues as described for tablets containing a single peptide. The final peptide concentration in the UPEC tablets is 1.4 mM PEG-Q11PepIreA, 1.4 mM PEG-Q11PepIutA, 1.4 mM PEG-Q11PepIroN, and 0.6 mM VACQ11 (or 0.6 mM Q11 for control tablets not containing the VAC T-cell epitope).

MicroCT: Analysis was performed using a Nikon XTH 225 ST instrument, with collection of 2500 projections and an exposure time of 500 ms. Raw data was reconstructed using the Nikon Feldkamp Cone Based CT algorithm and Nikon software. Avizo software was used for 3D reconstructions.

Thioflavin T (ThT) Binding: To measure β-sheet character, 20 μL of 2 mM peptide or dissolved tablet solutions were mixed with 180 μL of a 50 μM solution of ThT (Alfa Aesar, J61043) in 1×PBS in a black 96-well plate and read using a Molecular Devices Spectramax M2 spectrophotometer (excitation at 440 nm, emission at 488 nm).

Electron Microscopy: Transmission EM was performed as described.[8] For tablet imaging, tablets were dissolved in 1×PBS and samples were immediately prepared to avoid refibrillization.

Micro-Strain Analysis: Tablets were subjected to compressive testing at room temperature using a TA Instruments AIII microstrain-analyzer. The 15 mm size parallel plates corresponding to −81.8 gm±1.0 gm force were used. The diameter and height of each tablet was measured, and a compressive force was applied on each tablet for 360 seconds at an extension rate of −0.003 mm/sec.

In vitro Uptake Assay: DC2.4 mouse dendritic cells were seeded overnight in a 12 well plate at $1\times10^6$ cells/mL (1 mL per well) in complete RPMI media. The next day, 500 μL of media was aspirated and 500 μL of TAMRA-pOVA or media were added to pOVA-treated and untreated wells, respectively. For the tablet group, 500 μL of media was added to each well and the tablets were gently dropped into the wells to dissolve. All groups contained 20 nmol of total peptide per well. After incubation for 2 or 6 hours, the cells were prepared for flow cytometry. Cells were treated with Fc blocking antibody (BD Biosciences, cat # 553141) for 30 min and stained with CD11c:PE-Cy7 (BD Biosciences, cat #561022) for 30 min. Flow cytometry was performed on a FACS Canto cytometer and data was analyzed using FlowJo software.

Mice and Immunizations. Due to haplotype compatibility, female C57BL/6 mice (Envigo) were used for immunizations against pOVA and female CBA/J mice (Jackson Laboratory) were used for immunizations against ESAT6. Mice were 8-12 weeks at initiation of experiments (age matched within experiments). All animal experiments were performed under Duke University Institutional Care and Use Committee protocol A264-18-11. Sublingual immunizations were performed as previously describer[8]; for tablet groups, the tablets were placed under the anesthetized mouse's tongue using silicone-tipped tweezers. Peptide concentration, adjuvant dose, and boosting schedule are described in figure captions. KLH injections were performed as previously described.[22]

Antibody Measurement: Serum ELISAs were performed as previously described.[8] Briefly, plates were coated with streptavidin at 4° C. overnight, followed by incubation with biotin-pOVA, biotin-ESAT6, biotin-PepIreA, biotin-PepIutA, or biotin-PepIroN. Plates were blocked, diluted serum was added, and antigen-specific IgG was detected using goat anti-mouse IgG (Jackson Immuno Research, cat #115-035-071).

T-Cell Response Measurement: ELISPOT assays were performed essentially as described.[21] For analysis of lymph node responses, the submandibular and cervical nodes were taken as the draining lymph nodes. Antigen-specific stimulation was performed using the pOVA epitope.

Statistical Analysis: Statistical analysis was performed as indicated in figure legends using GraphPad Prism software. Means±standard error of the mean (s.e.m.) are presented. Statistically significant differences are indicated in each graph as $*p<0.05$, $p<0.01$, and $*p<0.001$.

Results

Figure 4:
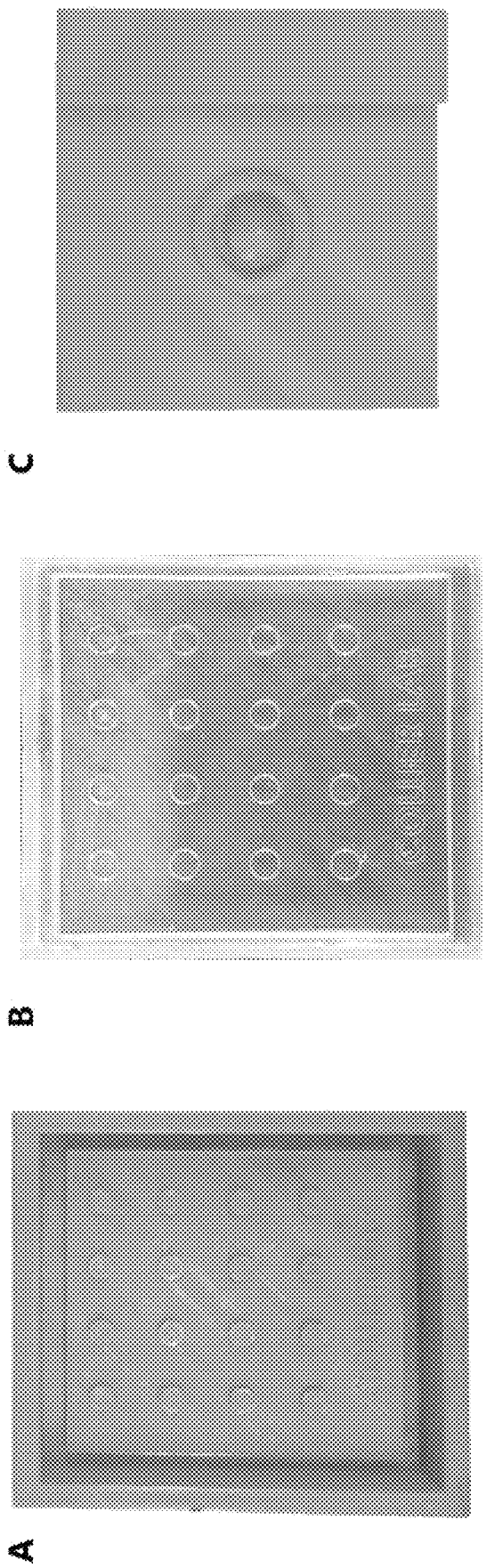
FIG. 4 shows photographs of the easy-to-make trays designed for the SIMPL tabletization process. (A) A reverse mold was 3D-printed using polylactic acid (PLA) filament. (B) The reverse mold was used to make the final tablet tray out of polydimethylsiloxane (PDMS). (C) A 3D-printed lid was designed to place on the mold during the freeze-drying process.

In designing a tablet vaccine, we sought to meet several key design criteria: (1) structural integrity for handleability, (2) microscale porosity for promoting dissolution, and (3) preservation of nanofiber structure for immunogenicity. We focused on a freeze-dried tabletization process, adopting the use of sugar excipients from pharmaceutical tablet production[9]. We selected mannitol and dextran to promote tablet strength and porosity[10-11] and trehalose as a cryoprotectant to aid in retaining nanofiber morphology.[12] We also included an adjuvant in the formulation due to our previous finding that this was needed for high-titer sublingual antibody responses with peptide nanofibers.[8] To control tablet size and shape, we 3D-printed a custom negative tablet mold, then made the final mold of flexible polydimethylsiloxane (PDMS) (FIG. 4). Freeze-dried SIMPL tablets were formed by mixing the sugars and adjuvant with fibrillized peptide-polymers, transferring the solution to the PDMS mold, and lyophilizing (FIG. 1A).

Figure 5:
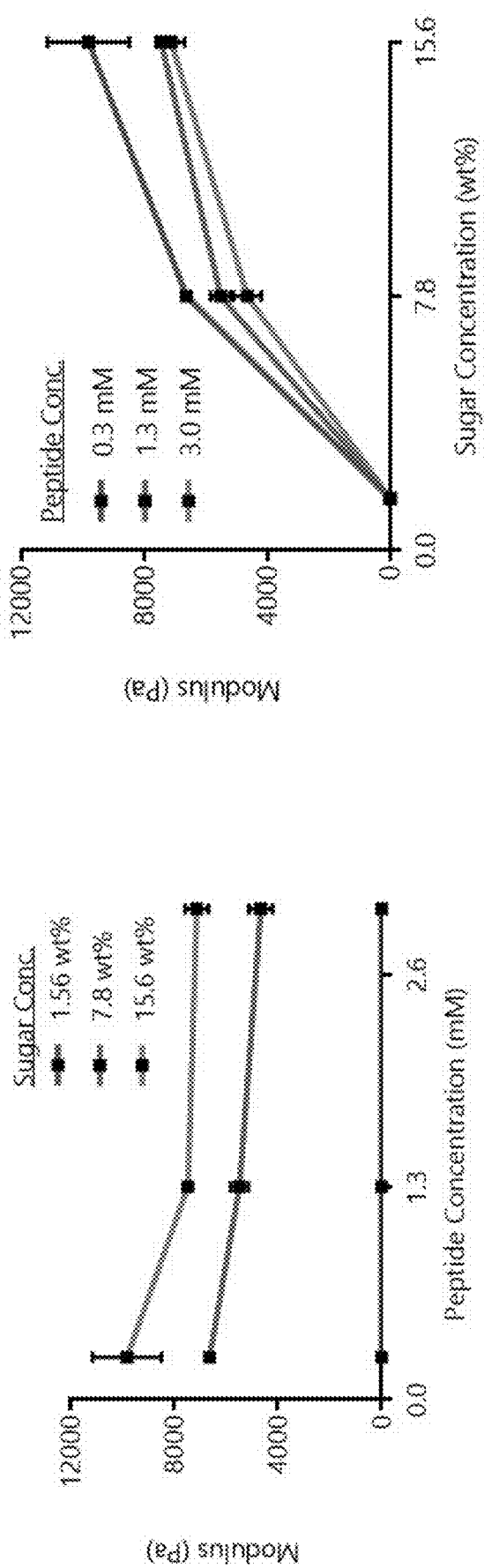
FIG. 5 shows the effect of changing sugar and peptide concentration on SIMPL tablet modulus. Individual graphs displaying the data used to generate the contour plot in FIG. 1D are shown. Tablets were prepared using nine combinations of peptide (OVAQ11-PEG$_{3000}$) and sugar (dextran and mannose) concentrations and subjected to compressive testing using a micro-strain analyzer. Trehalose concentration was held constant. A modulus of 0 Pa indicates that no tablet was formed under the given conditions.

The SIMPL tabletization process yielded tablets that were strong enough to be handled without breaking, fulfilling the bulk handleability requirement (FIG. 1B). An effective tablet should quickly dissolve in the volume-limited sublingual space. MicroCT analysis of the tablet's microstructure showed a high-degree of porosity qualitatively (FIG. 1C). This large surface-area allowed the tablets to dissolve rapidly in aqueous solvent. Further, by modulating the concentrations of peptide and sugar within the tabletized solutions, we could tune the elastic modulus of the resulting tablets (FIG. 1D, FIG. 5). Previous work in our lab has shown that fibrillization is critical to the function of Q11-based vaccines.[13] We used electron microscopy to compare the structure of nanofibers before and after tabletization (FIG. 1E-F). We immediately prepared TEM grids after dissolving tablets in PBS to prevent re-fibrillization over time from skewing the results. Nanofibers remained after tabletization, though they appeared slightly shorter by qualitative comparison. To corroborate this finding, we analyzed the extent of β-sheet secondary structure by Thioflavin T (ThT) binding (FIG. 1G). ThT binding was reduced after tabletization, but remained significantly higher than vehicle controls. Taken together, these findings suggested that although the tabletization process diminished nanofiber structure to some extent, significant fibrillar morphology was retained within SIMPL tablets.

Figure 2:
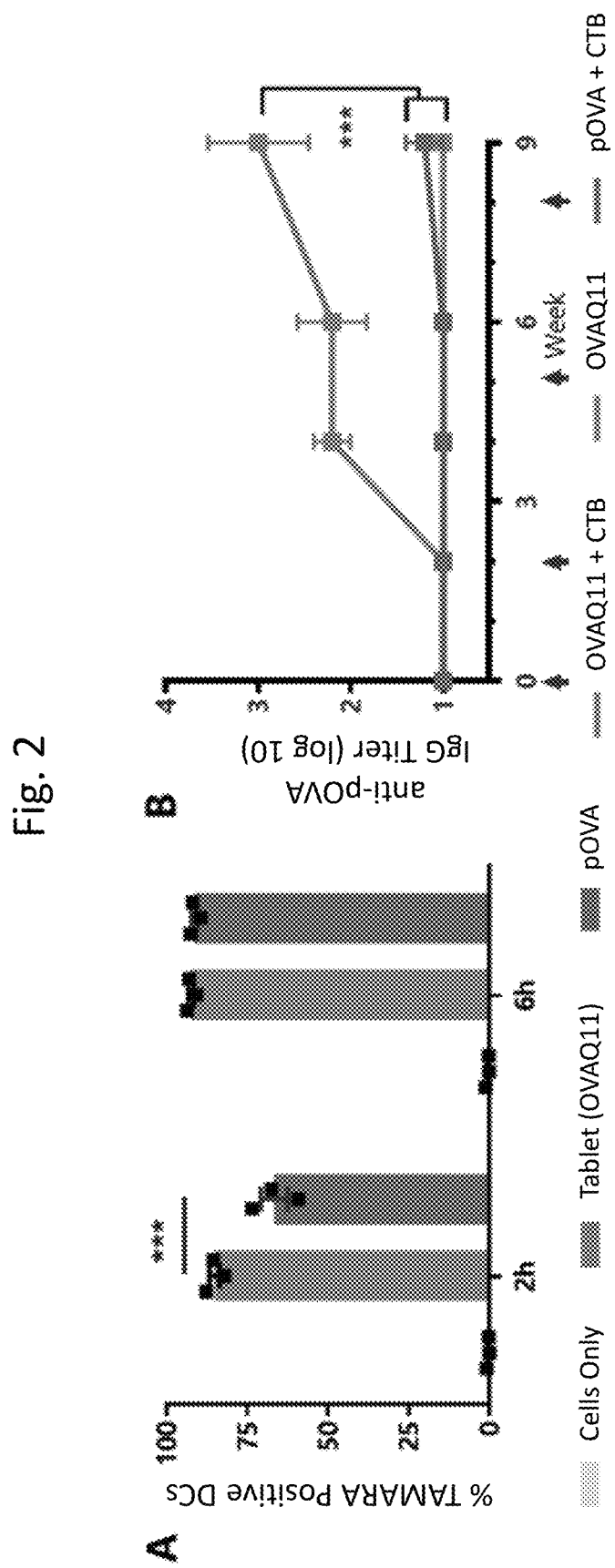
FIG. 2 demonstrates that SIMPL tablets containing Q11-PEG assemblies raise antibody responses in an adjuvant dose-dependent manner. (A) Fluorescently labelled TAMRA-pOVA peptide or SIMPL tablets prepared with TAMRA-OVAQ11 nanofibers were incubated with DC2.4 mouse dendritic cells, and uptake was measured by flow cytometry. *p<0.001 by 2-way ANOVA with Tukey's multiple comparisons test, n=3/group. (B) C57BL/6 mice were immunized sublingually with tablets containing 20 nmol of pOVA or OVAQ11 and 7 μg cholera toxin B adjuvant (CTB) and boosted at weeks 2, 5, and 8. *p<0.001 by 2-way ANOVA with Tukey's multiple comparisons test, n=5/group. (C) Mice from (B) were boosted at week 15 and sacrificed 7 days later. Spleens were harvested and T-cell responses were measured by ELISPOT. SFC: spot-forming cells. n.s. (not significant) by multiple 1-way ANOVAs, n=5/group. Full ELISPOT results are in FIG. 6. (D) Mice were immunized sublingually with tablets containing 20 nmol OVAQ11-PEG and 14 ug CTB and boosted at weeks 1, 5, and 17. n=5/group. (E) Mice from OVAQ11+CTB tablet groups in (B) and (D) were compared to show effect of adjuvant dose on titer. Color-coded arrows indicate boosting (black arrows indicate both groups were boosted). *p<0.05 by 2-way ANOVA. (F) Mice from (D) were sacrificed at week 18, spleens and draining lymph nodes (submandibular and cervical) were harvested, and T-cell responses were measured by ELISPOT. Full ELISPOT results are in FIG. 7. *p<0.05 by multiple t-tests with Holm-Šidák correction.
Figure 2:
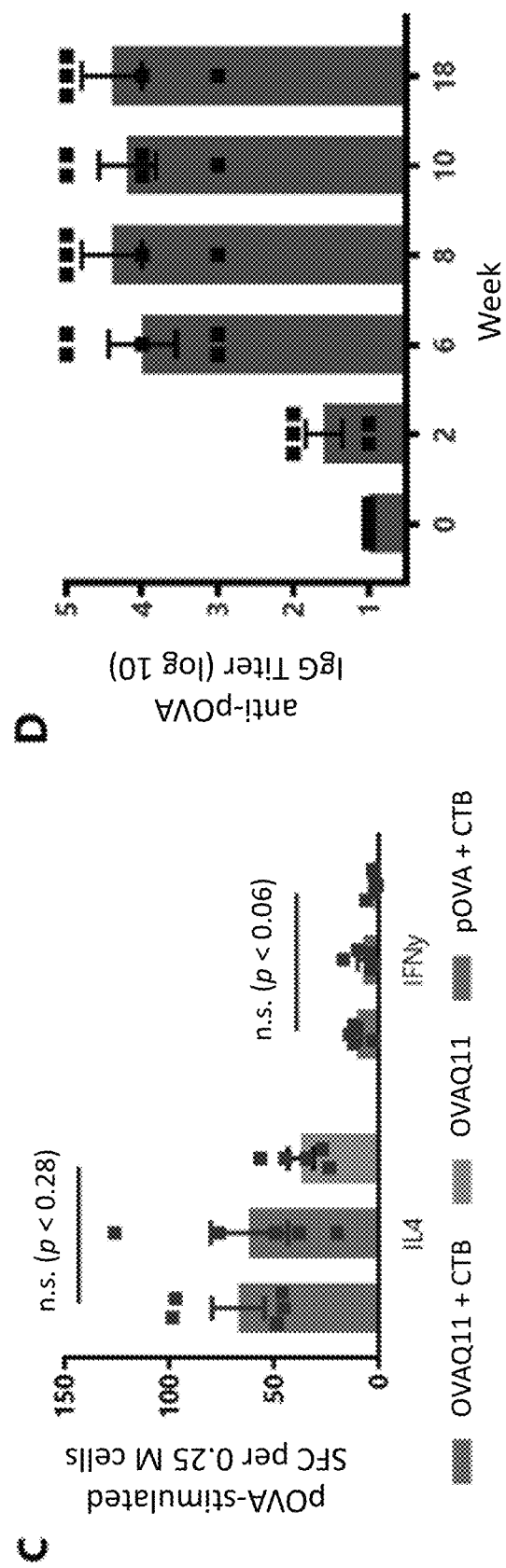
Figure 2:
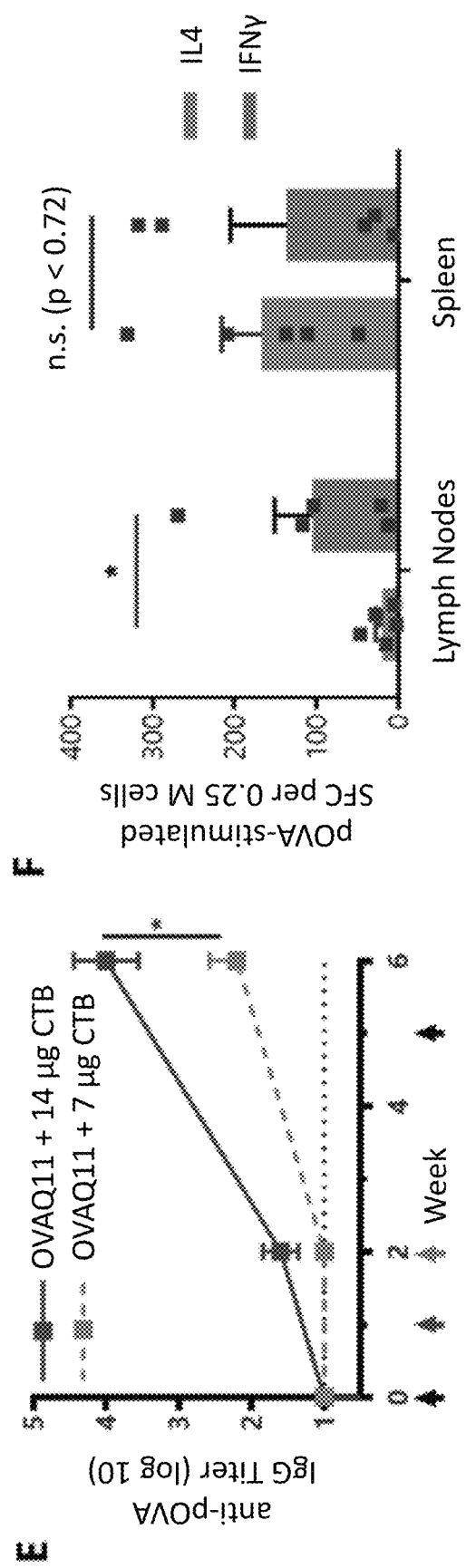
Figure 6:
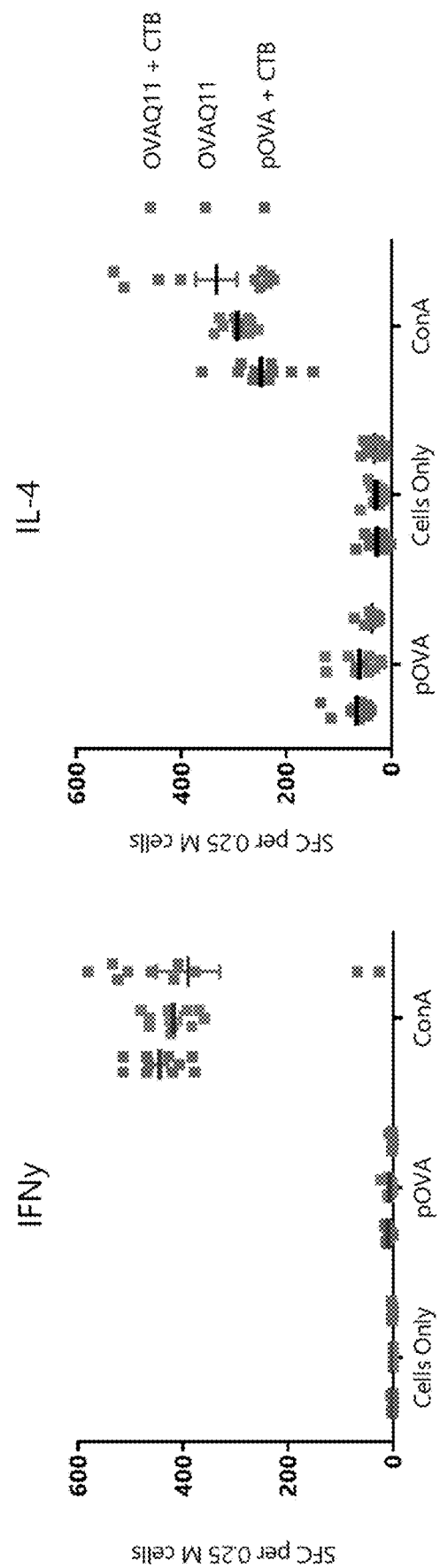
FIG. 6 shows the complete ELISPOT results for FIG. 2C. Mice were immunized sublingually with tablets containing 20 nmol of pOVA or OVAQ11 and 7 μg cholera toxin B adjuvant (CTB) and boosted at weeks 2, 5, 8, and 15. Mice were sacrificed at week 16 and spleens were harvested and analyzed by ELISPOT. Cells were either left unstimulated (as a negative control), stimulated with pOVA peptide (for antigen-specific response), or stimulated with ConA (as a positive control). Individual points represent two technical repeats that are averaged in FIG. 2C. n=5 mice/group.

We next sought to determine whether peptide nanofibers prepared in this way retained their immunogenicity. One advantage of supramolecular vaccines is their ability to raise antibody responses against peptide epitopes, which are highly specific but poorly immunogenic.[14] We first tested the ability of tabletized supramolecular assemblies to raise responses against the model $OVA_{323-339}$ peptide (pOVA). Co-assembled nanofibers containing both pOVA-Q11 and Q11-$PEG_{3000}$ were readily acquired when delivered to cultures of dendritic cells (FIG. 2A). For sublingual immunizations, we placed SIMPL tablets under the tongue of anesthetized C57BL/6 mice and allowed them to dissolve unaided (without the application of additional liquid). Mice immunized in this way with tablets containing nanofibers and the protein adjuvant cholera toxin B (CTB) raised epitope-specific IgG responses (FIG. 2B). Notably, tablets that contained PEG-conjugated pOVA (non-assembling) rather than self-assembling Q11OVA failed to raise responses, highlighting the importance of supramolecular assembly and suggesting the ability of the supramolecular tablet to preserve nanofiber structure. This is in line with previous work showing that assembly is essential for immunogenicity of subcutaneously delivered Q11 nanofibers[13] and sublingually delivered Q11-PEG solutions.[8] By contrast, T-cell responses were unaffected by the presence or absence of the Q11 assembly domain, with IL-4 dominant splenic responses observed for all groups (FIG. 2C, FIG. 6).

Figure 7:
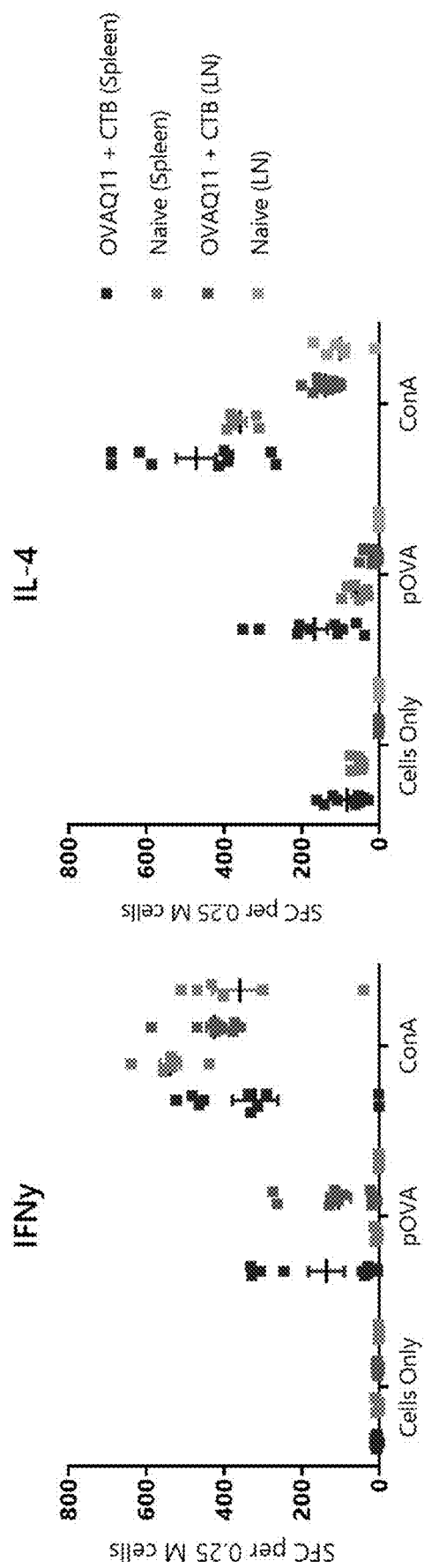
FIG. 7 shows the complete ELISPOT results for FIG. 2F. Mice were immunized sublingually with tablets containing 20 nmol OVAQ11 and 14 ug CTB and boosted at weeks 1, 5, and 17. Mice were sacrificed at week 18 and spleens and draining (submandibular and cervical) lymph nodes (LN) were harvested and analyzed by ELISPOT. Cells were either left unstimulated (as a negative control), stimulated with pOVA peptide (for antigen-specific response), or stimulated with ConA (as a positive control). Individual points represent two technical repeats that are averaged in FIG. 2F. n=5 mice/group (OVAQ11+CTB) or 3 mice/group (naive).

To test the ability to modulate the antibody titer raised by the SIMPL sublingual tablet vaccine, we increased the CTB adjuvant dose from 7 μg per tablet to 14 μg per tablet (FIG. 2D). Mice immunized with the higher adjuvant dose had significantly higher serum IgG titers after two boosts, with an increase in mean titer from 2.2 to 4, representing an over 60-fold change in antibody concentration (FIG. 2E). The higher dose of CTB adjuvant also led to T-cell responses that were more balanced between IL-4 and IFNγ in the spleen (FIG. 2F, FIG. 7), similar to previously published CTB-adjuvanted sublingual vaccines.[15] It is possible that at lower adjuvant doses, the Th2-bias of unadjuvanted Q11 vaccines[16] remains, but that at higher doses the effects of CTB are more pronounced. In contrast to the spleen, T-cell responses in the draining submandibular and cervical lymph nodes were more biased towards IFNγ (FIG. 2F). This is perhaps due to CTB adjuvant draining to the lymph node, but future characterization of the T-cell response to SIMPL tablets is needed to address these questions.

Having established the immunogenicity of SIMPL tablets, we next investigated the important consideration of heat stability. Given the importance of thermal stability to equitable global vaccine distribution, we chose a peptide epitope from *M. tuberculosis*. Tuberculosis is the leading cause of infectious death globally, with 97% of cases coming from low- and middle-income countries.[17] The selected peptide epitope from the 6 kDa early secretory antigenic target of *M. tuberculosis* (ESAT6) contains contiguous B- and T-cell epitopes and was a protective target in a preclinical model of tuberculosis infection.[18] In all experiments, heated groups were kept for one week at 45° C., a temperature at which even relatively stable vaccines can lose potency.[19-20]

Figure 3:
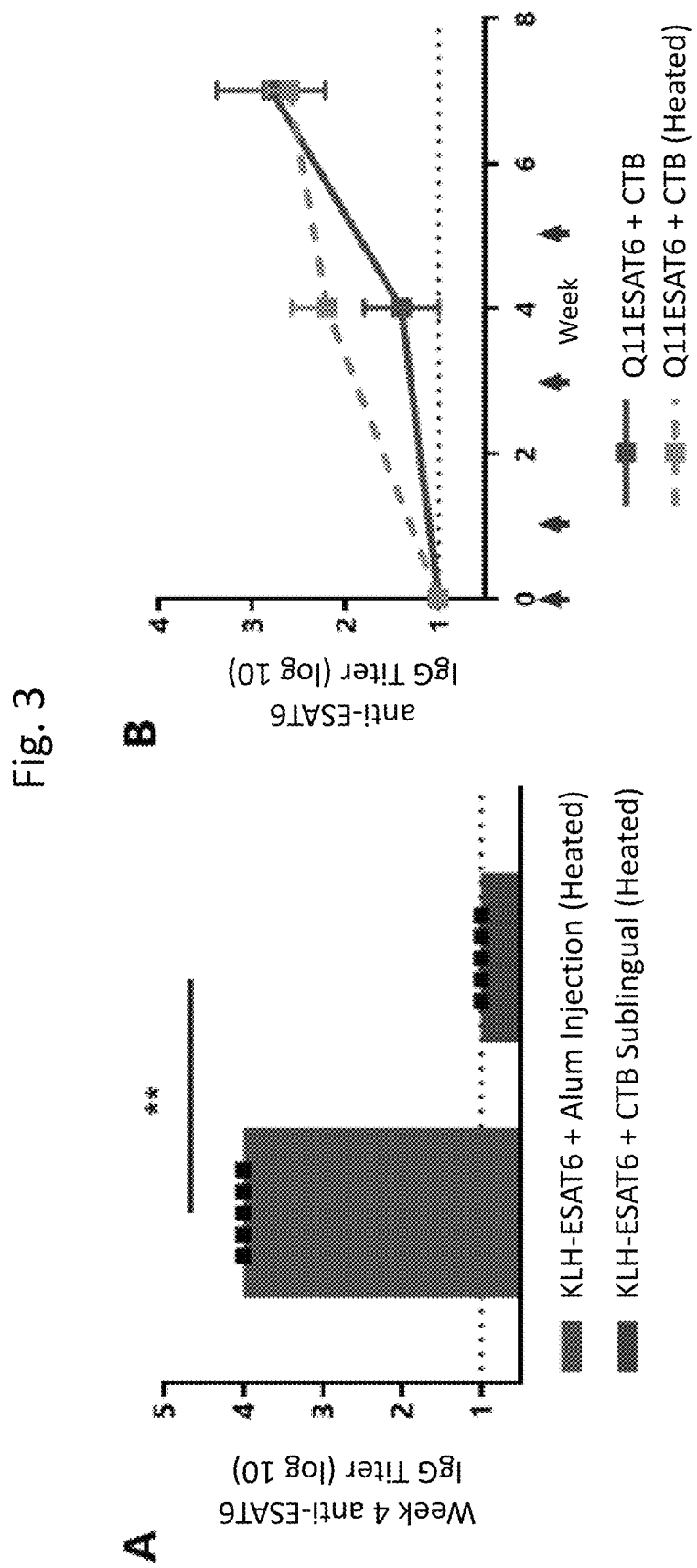
FIG. 3 demonstrates that the SIMPL tablet vaccine raises antibody responses against *M. tuberculosis* peptide epitope that are not diminished by heating. (A) CBA/J mice were immunized subcutaneously with a 1:1 mixture of alum and KLH-ESAT6 or sublingually with KLH-ESAT6 and 10 μg CTB and boosted at week 3. Heated group was heated at 45° C. for 7 days. **p<0.01 by 1-way ANOVA with Tukey's multiple comparisons test, n=5/group. (B) Mice were immunized with SIMPL tablets containing 20 nmol Q11ESAT6 and 10 μg CTB or cyclic-di-AMP adjuvant and boosted at weeks 1, 3, and 6. n=5/group. (C) Comparison of groups from (A) and (B). All groups were boosted at weeks 1, 3, and 6 and week 7 titer is shown. n.s. (not significant) or *p<0.05 by 1-way ANVOA with Tukey's multiple comparisons test, n=5/group. (D-E) Mice were immunized sublingually with KLH-ESAT6 or Q11ESAT6 and 15 μg CTB or AMP adjuvant and boosted at weeks 1, 3, 9, and 12. Heated groups were heated at 45° C. for 7 days. *p<0.05, **p<0.01 by 2-way ANOVA with Tukey's multiple comparisons test, n=5/group. (F) Serum IgG titers of heated and non-heated (NH) formulations from (D) and (E) were compared. n.s. (not significant), *p<0.01, ***p<0.001 by multiple t-tests with Holm-Šidák correction, n=5/group.
Figure 3:
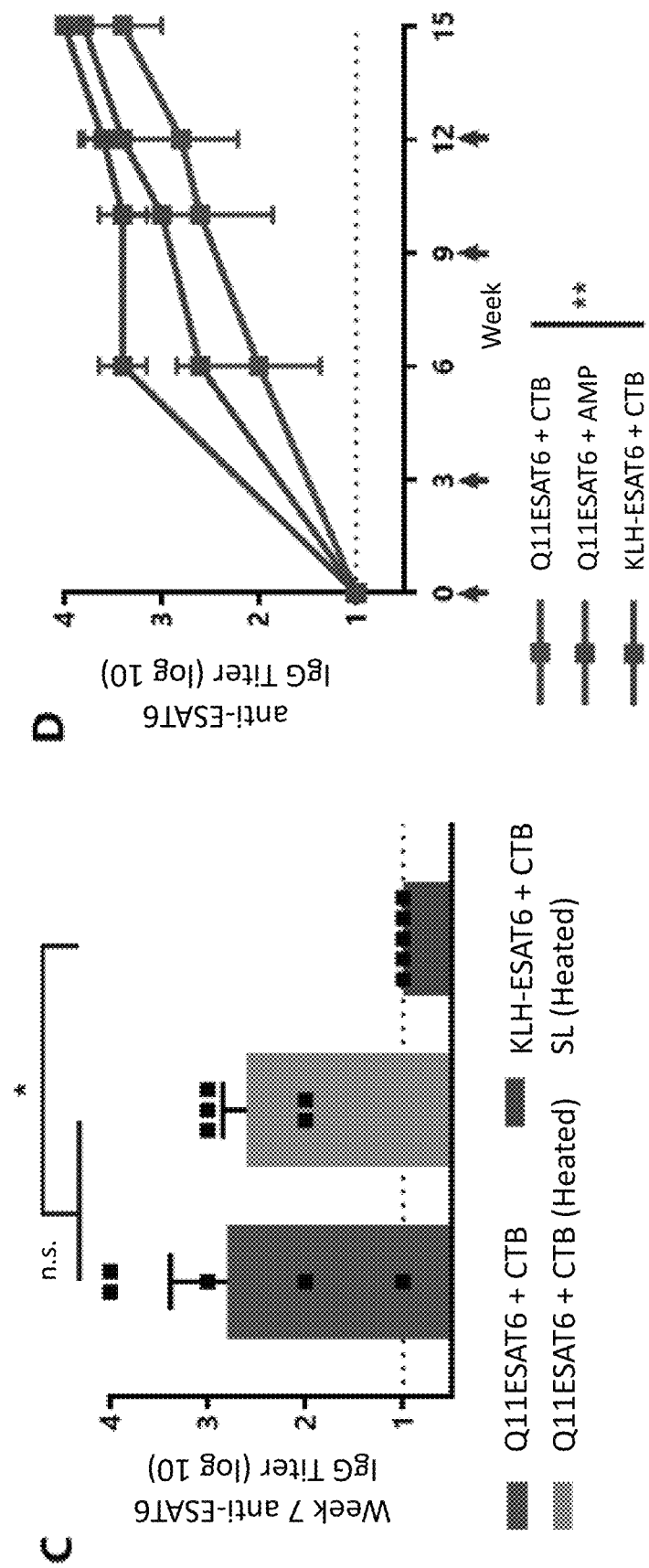
Figure 3:
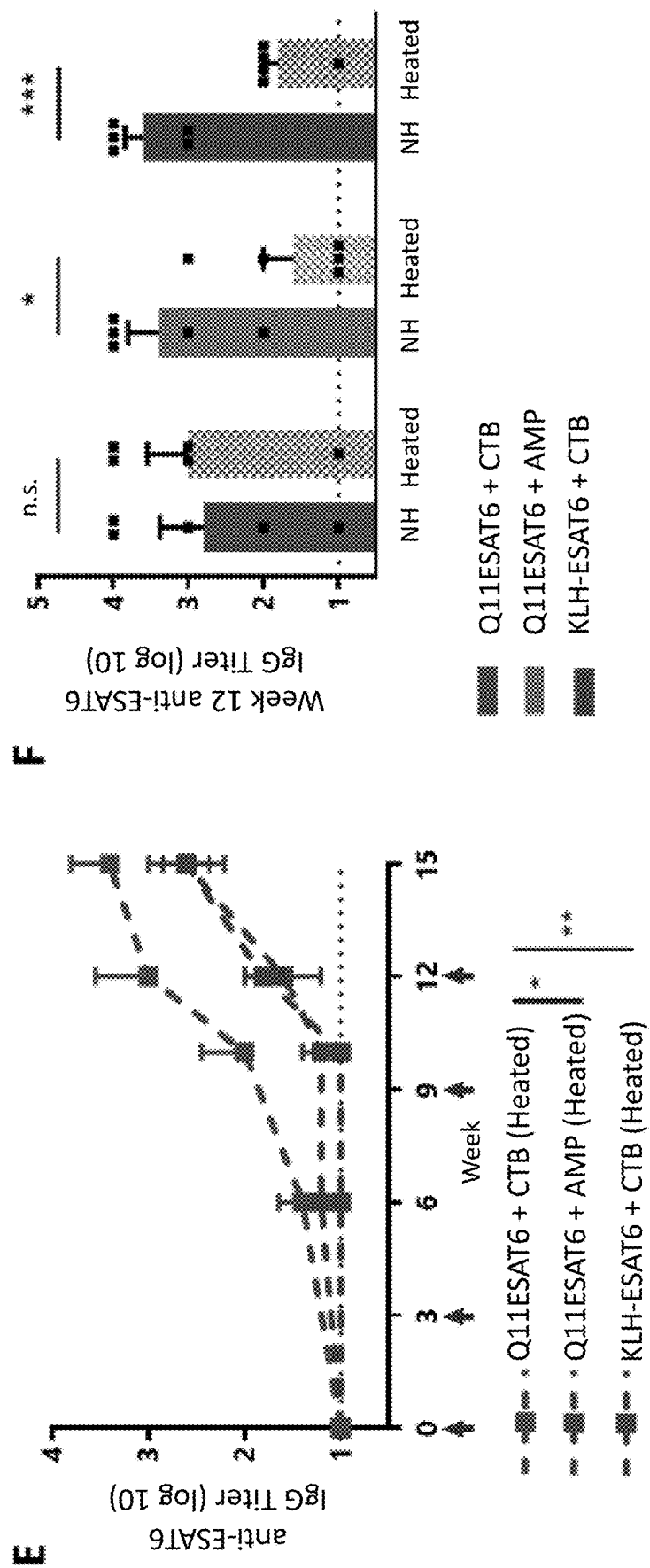

We compared the thermal stability of the tablet vaccine with a conventional peptide-carrier conjugate, keyhole limpet hemocyanin (KLH). Subcutaneous injection of CBA/J mice with KLH-ESAT6 and alum adjuvant led to strong antigen-specific antibody responses even after heating (FIG. 3A). Strikingly, however, sublingually delivered KLH-ESAT6 with CTB adjuvant led to no detectable response after heating, highlighting the challenge of sublingual peptide immunization. By contrast, sublingual immunization with heated SIMPL tablets containing $mPEth_{2000}$-Q11ESAT6 nanofibers (Q11ESAT6) and CTB adjuvant raised IgG antibodies (FIG. 3B). Most notably, there was no significant difference in response for mice immunized with heated or non-heated Q11ESAT6+CTB tablets (FIG. 3C).

To confirm and extend these findings, we repeated this experiment and tested the use of the nucleotide adjuvant cyclic-di-AMP. We also included a higher dose of adjuvant due to its ability to modulate titers in the tablet immunizations against the pOVA epitope (FIG. 2E). Sublingually delivered, non-heated KLH-ESAT6+CTB raised responses that were the same as tablets adjuvanted with cyclic-di-AMP and slightly higher than tablets adjuvanted with CTB (FIG. 3D). The results were dramatically different after heating, however, as CTB-adjuvanted tablets elicited significantly greater antibody levels than the KLH-based vaccine (FIG. 3E). We again found that SIMPL tablets containing ESAT6Q11+CTB were completely unaffected by heating, while KLH+CTB responses were significantly reduced (FIG. 3F). Interestingly, tablets containing cyclic-di-AMP adjuvant were not heat-stable, indicating that adjuvant stability is an important consideration even when using a heat-stable vaccine platform.

Figure 8:
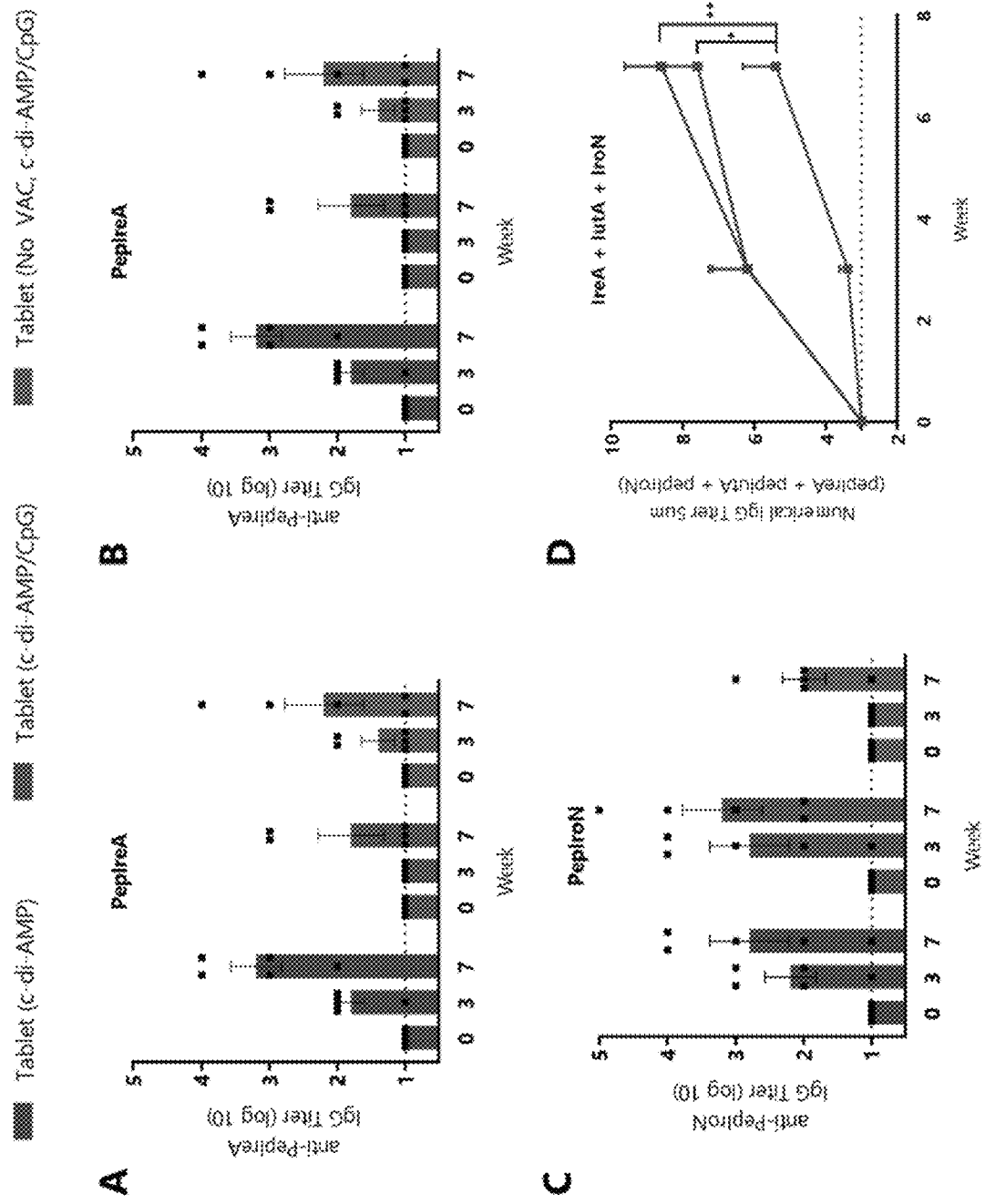
FIG. 8 demonstrates that a single sublingually delivered tablet vaccine raises T-cell dependent antibody responses against multiple B-cell epitopes from uropathogenic *E. coli*. Female C57BL/6 mice were immunized sublingually with a tablet containing 1.4 mM PEG-Q11PepIreA (A), 1.4 mM PEG-Q11PepIutA (B), 1.4 mM PEG-Q11PepIroN (C), and 0.6 mM VACQ11, with or without 10 μg of cyclic-di-AMP (c-di-AMP) or CpG adjuvant, and boosted at weeks 2 and 6. Control tablets (No VAC) have 0.6 mM Q11 in place of VACQ11, and thus lack a T-cell epitope. Serum antibody titers were measured by ELISA against each of the epitopes. *p<0.05, **p<0.01, 2-way ANOVA with Tukey's multiple comparisons, n=5 mice/group.
Figure 9:
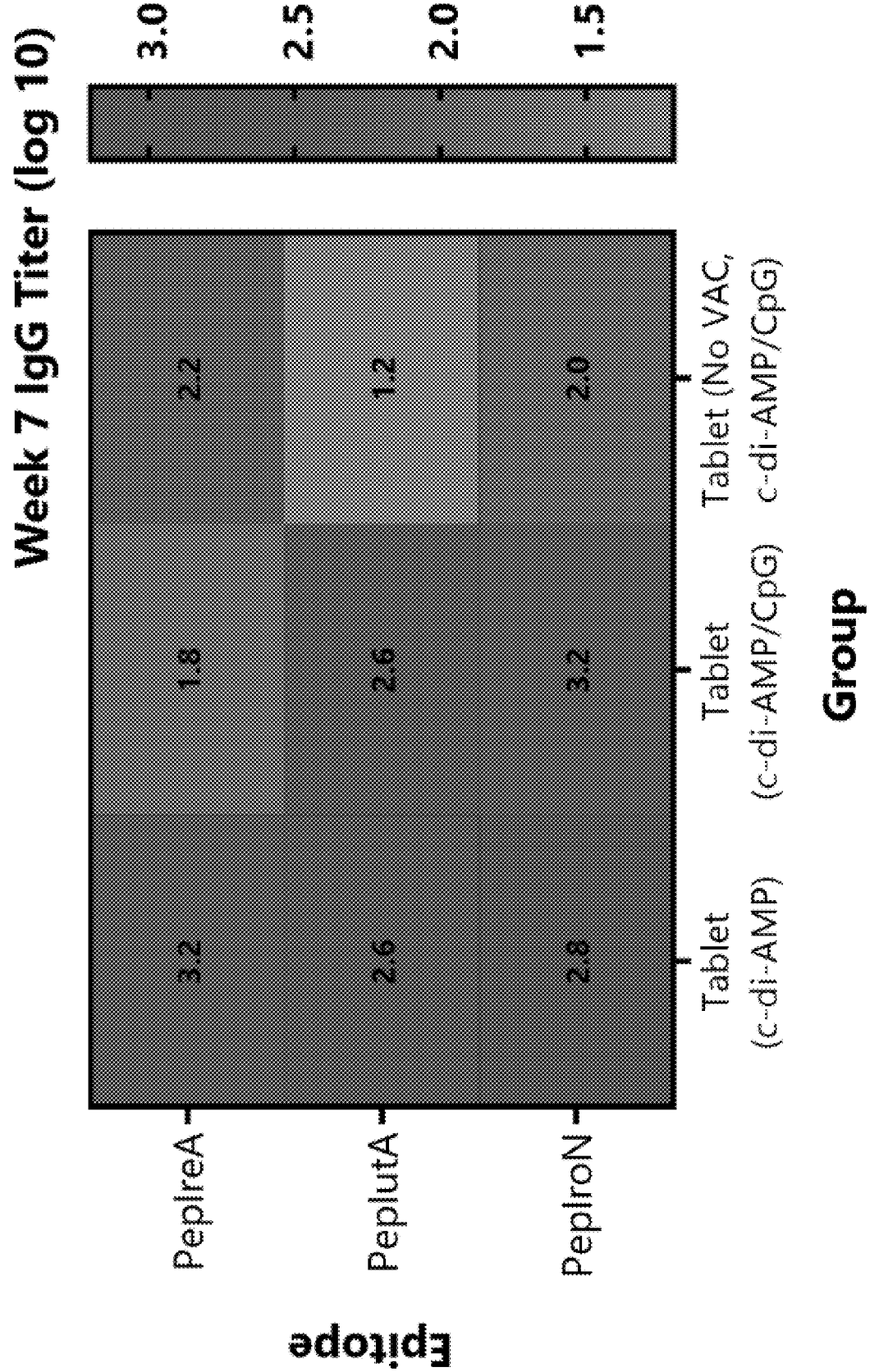
FIG. 9 shows a comparison of antibody distribution after sublingual immunization with tablet vaccine against three epitopes from uropathogenic *E. coli*. Female C57BL/6 were immunized sublingually with a tablet containing 1.4 mM PEG-Q11PepIreA, 1.4 mM PEG-Q11PepIutA, 1.4 mM PEG-Q11PepIroN, and 0.6 mM VACQ11, with or without 10 μg of cyclic-di-AMP (c-di-AMP) or CpG adjuvant, and boosted at weeks 2 and 6. Control tablets (No VAC) have 0.6 mM Q11 in place of VACQ11, and thus lack a T-cell epitope. Serum antibody titers were measured by ELISA against each of the epitopes.
Figure 10:
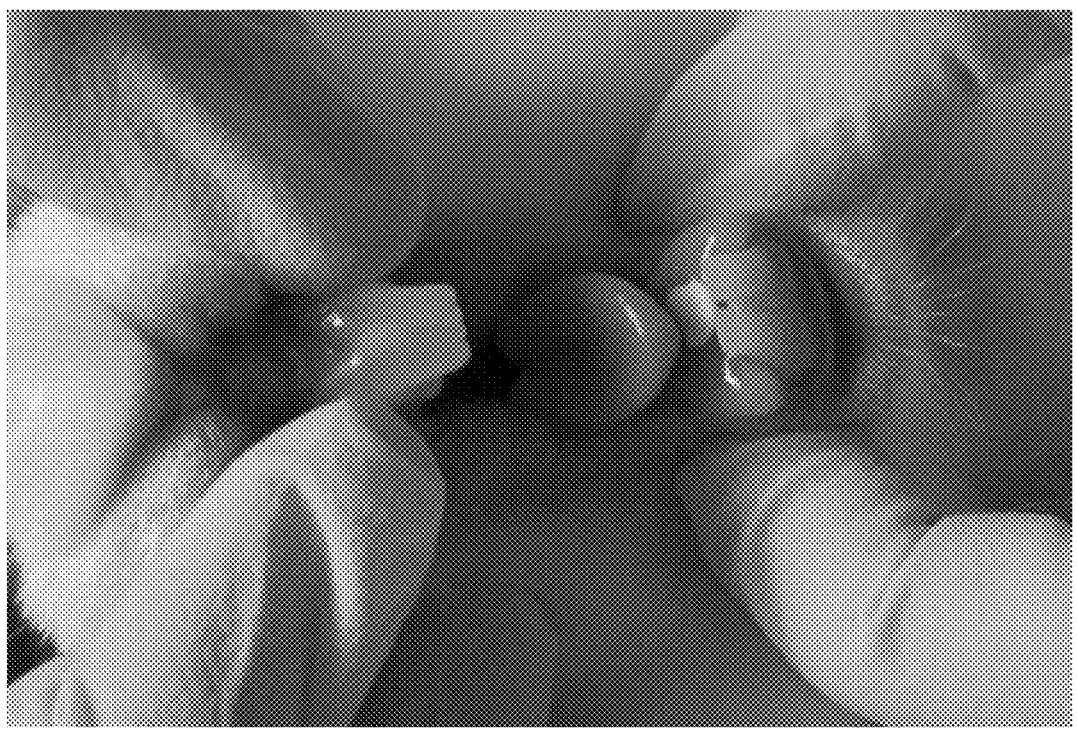
FIG. 10 is a photograph showing administration of sublingual tablet vaccine to rabbits. Tablets are placed below the tongue of anesthetized rabbits and allowed to dissolve unaided to deliver the vaccine material.
Figure 11:
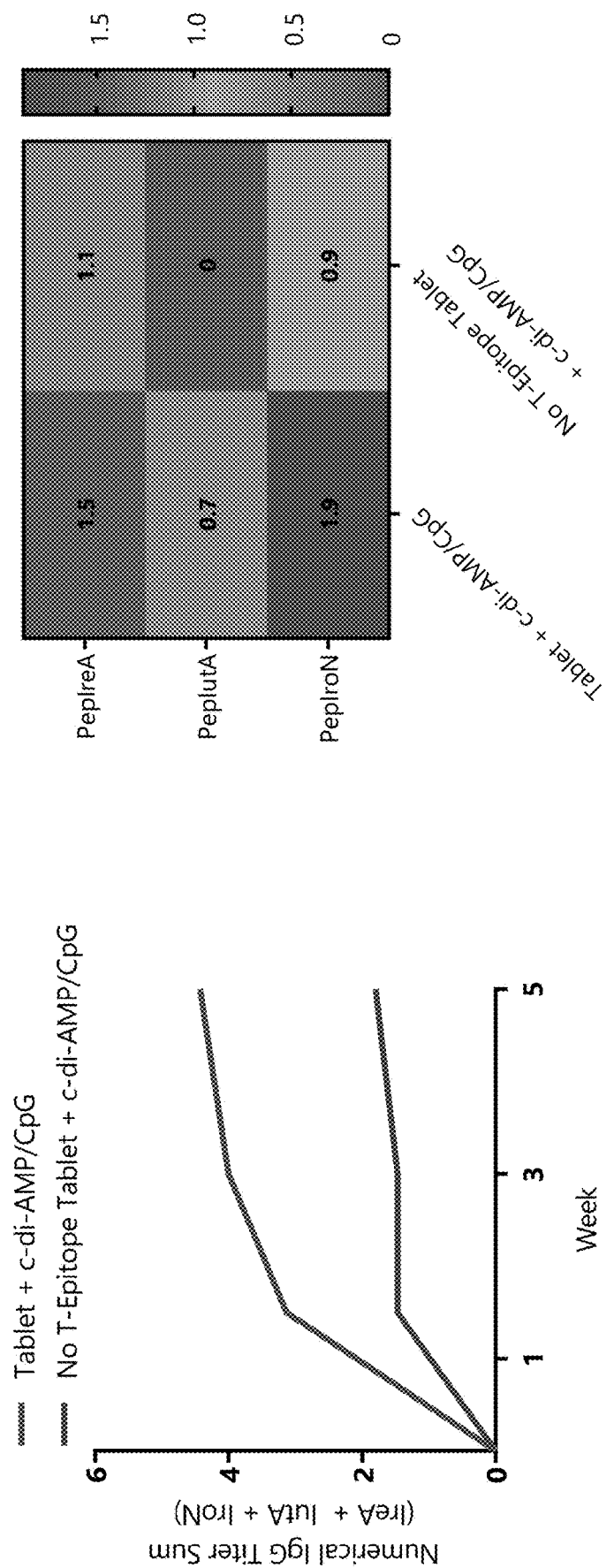
FIG. 11 demonstrates that a single sublingually delivered tablet vaccine raises T-cell dependent antibody responses against multiple UPEC-derived B-cell epitopes in rabbits. Female New Zealand White rabbits were immunized sublingually with tablets containing 1.4 mM PEG-Q11PepIreA, 1.4 mM PEG-Q11PepIutA, 1.4 mM PEG-Q11PepIroN, and 0.6 mM VACQ11, with 10 μg of cyclic-di-AMP (c-di-AMP) and 25 ug of CpG. Rabbits were boosted at weeks 2 and 4. Control (no T-epitope) tablets have 0.6 mM Q11 in place of VACQ11. Serum antibody titers were measured by ELISA against each of the epitopes. In the left panel, bold lines represent the mean titer and faded lines represent individual rabbits.

Finally, to demonstrate the versatility of this novel vaccine platform, we generated SIMPL sublingual tablets comprising three B-cell epitopes from uropathogenic *E. coli* (UPEC; see Table 3 for peptide sequences). Female C57BL/6 mice were immunized sublingually with tablets containing 1.4 mM of each nanofiber-antigen combination, with or without 10 μg of cyclic-di-AMP (c-di-AMP) or CpG adjuvant, and boosted at weeks 2 and 6. Immunization with the tablets was found to raise T-cell dependent antibody responses against all three B-cell epitopes (FIG. 8), although the antibody distribution varied across epitopes (FIG. 9) To provide a more relevant test of the translational potential of SIMPL tablets, we immunized NZW white rabbits with identically formulated UPEC tablets as those used in mice (FIG. 10). The human oral cavity is more similar to that of rabbits than mice, with both rabbits and humans having non-keratinized sublingual epithelia and each containing more cell layers within the epithelia than mice. Preliminary results from immunization of rabbits with SIMPL tablets showed that serum IgG responses could be raised against multiple peptide epitopes in rabbits (FIG. 11). Comparison of human, mouse and oral cavities can be found in Thirion-Delalande, C et. al. Comparative analysis of the oral mucosae from rodents and non-rodents: Application to the non-clinical evaluation of sublingual immunotherapy products. PloS one 2017, the contents of which are incorporated by reference.

Conclusions

In summary, we designed a sublingual tablet vaccine based on self-assembling peptide-polymer nanofibers. These SIMPL tablets represent the first demonstration of a nanomaterial sublingual tablet vaccine to our knowledge. Through addition of sugar excipients and freeze-drying, the tabletization process produced highly porous and easily handleable tablets that raise antibody responses against both the model epitope pOVA and the *M. tuberculosis* epitope ESAT6. The tablets were easily administrable by dissolving under the tongue. In contrast to a conventional KLH-based vaccine, sublingually delivered tablets with CTB adjuvant were heat-stable and showed no loss of immunogenicity after heating at 45° C. for one week. Cyclic-di-AMP adjuvanted tablets did show some loss of potency after heating. Exploring the use of alternate adjuvants or modifications to the tabletization process to preserve the effects of thermally sensitive adjuvants is an interesting area for future work. The thermal stability of SIMPL tablets, combined with their potential for self-administration, shows exciting potential for improving equitable global vaccine distribution.

TABLE 2

Sequences of peptides used in this study.

| Peptide | Sequence | Function |
|---|---|---|
| OVAQ11-PEG$_{3000}$ | H$_2$N-ISQAVHAAHAEINEAGRSGSGQQKFQFQFEQQ-CH$_2$CH$_2$—(CH$_2$CH$_2$O)$_n$-OH (SEQ ID NO: 81; Average n = 68) | Model B- and T-cell epitope |
| pOVA | H$_2$N-ISQAVHAAHAEINEAGR-NH$_2$ (SEQ ID NO: 82) | Non-assembling control model B- and T-cell epitope |
| pOVA-PEG$_{3000}$ | H$_2$N-ISQAVHAAHAEINEAGR-COCH$_2$CH$_2$—(CH$_2$CH$_2$O)$_n$-H (SEQ ID NO: 82; Average n = 68) | Non-assembling, PEGylated, control model B- and T-cell epitope |
| C-ESAT6 | H$_2$N-CYQGVQQKWDATATELNNALQ-NH$_2$ (SEQ ID NO: 83) | Cysteine-appended *M. tuberculosis* B-and T-cell epitope for conjugation to KLH carrier protein |
| mPEG$_{2000}$-Q11ESAT6 | CH$_3$O—(CH$_2$CH$_2$O)$_n$-SGSGQQKFQFQFEQQSGSGCYQGVQQKWDATATELNNALQ-NH$_2$ (SEQ ID NO: 84; Average n = 45) | *M. tuberculosis* B-and T-cell epitope |

TABLE 3

Components of sublingual tablet vaccine against uropathogenic *E. coli* (UPEC).

| Name | Sequence | Function |
|---|---|---|
| mPEG$_{2000}$-Q11PepIroN | CH$_3$O—(CH$_2$CH$_2$O)$_n$-SGSGQQKFQFQFEQQSGSG-YLLYSKGNGCPKDITSGGCYLIGNKDLDPE-NH$_2$ (SEQ ID NO: 85) | UPEC B-cell epitope |

TABLE 3-continued

Components of sublingual tablet vaccine against uropathogenic E. coli (UPEC).

| Name | Sequence | Function |
| --- | --- | --- |
| mPEG$_{2000}$-Q11PepIutA | CH$_3$O—(CH$_2$CH$_2$O)$_n$-SGSG-QQKFQFQFEQQSGSG-VDDIDYTQQQKIAAGKAISADAIPGGSVD-NH$_2$ (SEQ ID NO: 86) | UPEC B-cell epitope |
| mPEG$_{2000}$-Q11PepIreA | CH$_3$O—(CH$_2$CH$_2$O)$_n$-SGSGQQKFQFQFEQQ-SGSG-GIAKAFRAPSIREVSPGFGTLTQGGASIMYGN-NH$_2$ (SEQ ID NO: 87) | UPEC B-cell epitope |
| VACQ11 | NH$_2$-QLVFNSISARALKAYSGSGQQKFQFQFEQQ-NH$_2$ (SEQ ID NO:88) | T-helper epitope |

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

REFERENCES

[1] Peck, M.; Gacic-Dobo, M.; Diallo, M. S.; Nedelec, Y.; Sodha, S. S.; Wallace, A. S., Global Routine Vaccination Coverage, 2018. *Morbidity and Mortality Weekly Report* 2019, 68 (42), 937.
[2] De Boeck, K.; Decouttere, C.; Vandaele, N., Vaccine distribution chains in low-and middle-income countries: A literature review. *Omega* 2019.
[3] Ashok, A.; Brison, M.; LeTallec, Y., Improving cold chain systems: challenges and solutions. *Vaccine* 2017, 35 (17), 2217-2223.
[4] van den Ent, M. M.; Yameogo, A.; Ribaira, E.; Hanson, C. M.; Ratoto, R.; Rasolomanana, S.; Foncha, C.; Gasse, F., Equity and immunization supply chain in Madagascar. *Vaccine* 2017, 35 (17), 2148-2154.
[5] Reina, J., The sublingual influenza vaccine. *Vacunas (English Edition)* 2019.
[6] Kraan, H.; Vrieling, H.; Czerkinsky, C.; Jiskoot, W.; Kersten, G.; Amorij, J.-P., Buccal and sublingual vaccine delivery. *Journal of controlled release* 2014, 190, 580-592.
[7] Yenkoidiok-Douti, L.; Jewell, C. M., Integrating Biomaterials and Immunology to Improve Vaccines Against Infectious Diseases. *ACS Biomaterials Science & Engineering* 2020.
[8] Kelly, S. H.; Wu, Y.; Varadhan, A. K.; Curvino, E. J.; Chong, A. S.; Collier, J. H., Enabling sublingual peptide immunization with molecular self-assemblies. *Biomaterials* 2020, 119903.
[9] Wilkhu, J. S.; McNeil, S. E.; Anderson, D. E.; Kirchmeier, M.; Perrie, Y., Development of a solid dosage platform for the oral delivery of bilayer vesicles. *European Journal of Pharmaceutical Sciences* 2017, 108,71-77.
[10] Chandrasekhar, R.; Hassan, Z.; AlHusban, F.; Smith, A. M.; Mohammed, A. R., The role of formulation excipients in the development of lyophilised fast-disintegrating tablets. *European journal of pharmaceutics and biopharmaceutics* 2009, 72 (1), 119-129.
[11] Sastry, S. V.; Nyshadham, J. R.; Fix, J. A., Recent technological advances in oral drug delivery—a review. *Pharmaceutical science & technology today* 2000, 3 (4), 138-145.
[12] Ohtake, S.; Wang, Y. J., Trehalose: current use and future applications. *Journal of pharmaceutical sciences* 2011, 100 (6), 2020-2053.
[13] Rudra, J. S.; Sun, T.; Bird, K. C.; Daniels, M. D.; Gasiorowski, J. Z.; Chong, A. S.; Collier, J. H., Modulating adaptive immune responses to peptide self-assemblies. *Acs Nano* 2012, 6 (2), 1557-1564.
[14] Wen, Y.; Collier, J. H., Supramolecular peptide vaccines: tuning adaptive immunity. *Current opinion in immunology* 2015, 35, 73-79.
[15] Cho, H.-J.; Kim, J.-Y.; Lee, Y.; Kim, J. M.; Kim, Y. B.; Chun, T.; Oh, Y.-K., Enhanced humoral and cellular immune responses after sublingual immunization against human papillomavirus 16 L1 protein with adjuvants. *Vaccine* 2010, 28 (14), 2598-2606.
[16] Mora-Solano, C.; Wen, Y.; Han, H.; Chen, J.; Chong, A. S.; Miller, M. L.; Pompano, R. R.; Collier, J. H., Active immunotherapy for TNF-mediated inflammation using self-assembled peptide nanofibers. *Biomaterials* 2017, 149, 1-11.
[17] Organization, W. H., Global tuberculosis report. Geneva: World Health Organization, 2017. *Contract No.: WHO/HTM/TB* 2017.
[18] Weinreich Olsen, A.; Hansen, P. R.; Holm, A.; Andersen, P., Efficient protection against *Mycobacterium tuberculosis* by vaccination with a single subdominant epitope from the ESAT-6 antigen. *European journal of immunology* 2000, 30 (6), 1724-1732.
[19] Organization, W. H. *Temperature sensitivity of vaccines;* World Health Organization: 2006.
[20] Van Damme, P.; Cramm, M.; Safary, A.; Vandepapeliere, P.; Meheus, A., Heat stability of a recombinant DNA hepatitis B vaccine. *Vaccine* 1992, 10 (6), 366-367.
[21] Wu, Y.; Norberg, P. K.; Reap, E. A.; Congdon, K. L.; Fries, C. N.; Kelly, S. H.; Sampson, J. H.; Conticello, V. P.;

Collier, J. H., A Supramolecular Vaccine Platform Based on α-Helical Peptide Nanofibers. *ACS Biomaterials Science & Engineering* 2017, 3 (12), 3128-3132.

[22] Sun, T.; Han, H.; Hudalla, G. A.; Wen, Y.; Pompano, R. R.; Collier, J. H., Thermal stability of self-assembled peptide vaccine materials. *Acta biomaterialia* 2016, 30, 62-71.

What is claimed:

1. A dissolvable tablet formulation comprising
   (a) self-assembling peptide-polymer nanofibers comprising a peptide-polymer conjugate comprising
      (i) a self-assembling domain comprising a polypeptide and having a C-terminal and N-terminal end;
      (ii) a peptide epitope or protein antigen; and
      (iii) a mucus-inert domain, wherein (ii) and (iii) are linked opposite ends of the (i) self-assembling domain;
   (b) an excipient; and
   (c) an adjuvant,
   wherein the dissolvable tablet is suitable for sublingual administration.

2. The dissolvable tablet of claim 1, wherein the excipient is a sugar.

3. The dissolvable tablet of claim 1, wherein the dissolvable tablet is heat stable at 45° C. for at least a seven days.

4. The dissolvable tablet of claim 1, wherein the tablet has a suitable porosity such that the tablet is able to dissolve sublingually in less than a minute.

5. The dissolvable tablet of claim 1, wherein the self-assembling domain comprises a polypeptide of 5 to 40 amino acids.

6. The dissolvable tablet of claim 1, wherein the self-assembling domain comprises a polypeptide having an amino acid sequence selected from SEQ ID NOs: 1-67.

7. The dissolvable tablet of claim 1, wherein the self-assembling domain comprises a polypeptide having an amino acid sequence of SEQ ID NO: 1.

8. The dissolvable tablet of claim 1, wherein the polymer domain comprises polyethylene glycol (PEG), optionally wherein the PEG domain has an average molecular weight of 300-5000 Da.

9. The dissolvable tablet of claim 1, wherein the conjugate self-assembles into nanofibers.

10. The dissolvable tablet of claim 1, wherein the tablet elicits an antibody response upon or after administration to a subject sublingually.

11. The dissolvable tablet of claim 1, wherein the tablet elicits a T cell response upon or after administration to a subject sublingually.

12. The dissolvable table of claim 1, wherein the epitope peptide or the protein antigen is a bacterial, viral or fungal epitope peptide or protein antigen.

13. A method of eliciting an immune response against a peptide or protein antigen in a subject, the method comprising administering a therapeutically effective amount of the dissolvable tablet of claim 1 sublingually to the subject.

14. A method of formulating a vaccine comprising dissolvable sublingual tablet, the method comprising the steps of:
   (i) combining self-assembling a peptide-polymer conjugate with a buffer to form a peptide-polymer nanofiber;
   (ii) adding at least one excipient and an adjuvant to the peptide-polymer nanofiber to form a vaccine solution;
   (iii) placing the vaccine solution into a mold; and
   (iv) removing the liquid from the vaccine solution to produce a tablet.

15. The method of claim 14, wherein step (iv) comprises freezing and lyophilizing the solution to produce the tablet.

16. The method of claim 14, wherein the peptide-polymer conjugate comprises (i) a self-assembling domain comprising a polypeptide and having a C-terminal and N-terminal end; (ii) a peptide epitope or protein antigen; and (iii) a polymer domain, wherein the peptide epitope or protein antigen and the polymer are linked to the opposite ends of the self-assembling domain.

17. The method of claim 14, wherein step (ii) further comprises adding a cryoprotectant to form the vaccine solution.

18. A vaccine formulated in tablet form produced by the method according to claim 14.

19. The vaccine according to claim 18 in which the vaccine is specific for a bacteria, a virus or a fungus.

20. The vaccine according to claim 19 in which the vaccine comprises the epitope $ESAT_{51-70}$ for *M. tuberculosis*.

* * * * *